United States Patent
Jung et al.

(10) Patent No.: US 11,957,741 B2
(45) Date of Patent: *Apr. 16, 2024

(54) LONG LASTING EFFECT OF NEW BOTULINUM TOXIN FORMULATIONS

(71) Applicant: Medy-Tox, Inc., Suwon-si (KR)

(72) Inventors: Hyun Ho Jung, Seoul (KR); Gi Hyeok Yang, Cheonan-si (KR); Hyun Jee Kim, Asan-si (KR); Chang Hoon Rhee, Seoul (KR)

(73) Assignee: MEDY-TOX, INC., Chungchongbuk-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/155,301

(22) Filed: Jan. 17, 2023

(65) Prior Publication Data

US 2023/0149520 A1    May 18, 2023

Related U.S. Application Data

(60) Continuation of application No. 17/011,824, filed on Sep. 3, 2020, now Pat. No. 11,596,673, which is a continuation of application No. 16/207,387, filed on Dec. 3, 2018, now Pat. No. 11,590,212, which is a division of application No. 15/336,119, filed on Oct. 27, 2016, now Pat. No. 10,143,728, which is a continuation of application No. 14/567,289, filed on Dec. 11, 2014, now Pat. No. 9,480,731.

(60) Provisional application No. 61/915,476, filed on Dec. 12, 2013.

(51) Int. Cl.
| | |
|---|---|
| *A61K 8/64* | (2006.01) |
| *A61K 8/66* | (2006.01) |
| *A61K 9/00* | (2006.01) |
| *A61K 9/19* | (2006.01) |
| *A61K 38/48* | (2006.01) |
| *A61Q 19/08* | (2006.01) |

(52) U.S. Cl.
CPC ............ *A61K 38/4893* (2013.01); *A61K 8/64* (2013.01); *A61K 8/66* (2013.01); *A61K 9/0019* (2013.01); *A61K 9/19* (2013.01); *A61Q 19/08* (2013.01); *C12Y 304/24069* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 7,226,605 | B2 | 6/2007 | Suskind et al. |
| 7,829,525 | B2 | 11/2010 | Frevert |
| 8,137,677 | B2 | 3/2012 | Hunt |
| 8,580,745 | B2 | 11/2013 | Borodic |
| 8,617,568 | B2 | 12/2013 | Jung et al. |
| 8,921,322 | B2 | 12/2014 | Favre et al. |
| 9,050,246 | B2 | 6/2015 | Bertholon et al. |
| 9,072,779 | B2 | 7/2015 | Petrella |
| 9,125,804 | B2 | 9/2015 | Webb et al. |
| 9,480,731 | B2 | 11/2016 | Jung et al. |
| 10,143,728 | B2 | 12/2018 | Jung et al. |
| 10,561,604 | B2 | 2/2020 | Webb et al. |
| 10,772,943 | B2 | 9/2020 | Lee et al. |
| 2003/0118598 | A1 | 6/2003 | Hunt |
| 2003/0224020 | A1 | 12/2003 | Zabudkin et al. |
| 2006/0018931 | A1 | 1/2006 | Taylor |
| 2007/0134199 | A1 | 6/2007 | Frevert |
| 2008/0069841 | A1 | 3/2008 | Panjwani et al. |
| 2010/0168023 | A1 | 7/2010 | Ruegg et al. |
| 2010/0291136 | A1 | 11/2010 | Jung et al. |
| 2010/0330123 | A1 | 12/2010 | Thompson et al. |
| 2011/0092682 | A1 | 4/2011 | Ruegg |
| 2012/0107361 | A1 | 5/2012 | Thompson et al. |
| 2019/0183988 | A1 | 6/2019 | Jarstad et al. |
| 2020/0164050 | A1 | 5/2020 | Webb et al. |
| 2020/0383894 | A1 | 12/2020 | Pickett et al. |
| 2020/0397875 | A1 | 12/2020 | Jung et al. |
| 2021/0330766 | A1 | 10/2021 | Thompson et al. |

FOREIGN PATENT DOCUMENTS

| | | |
|---|---|---|
| EP | 2692350 A2 | 2/2014 |
| EP | 3079714 A1 | 10/2016 |
| KR | 1020120112248 A | 10/2012 |
| WO | 20070044809 A2 | 4/2007 |
| WO | 2009008595 A1 | 1/2009 |
| WO | 2010090677 A1 | 8/2010 |
| WO | 2012048854 A2 | 4/2012 |

OTHER PUBLICATIONS

Andrew Pickett, Employment agreement pp. 1-12; PGR2019-00062.
CV_Andreas Rummel; IPR2021-01203.
CV_Andrew Martin Pickett; PGR2019-00062.
CV_Ash Ramzan, Ph.D; PGR2019-00062.
CV_Ashwani K. Singh; PGR2019-00062.
CV_Charles Russell Middaugh, Ph.D.; PGR2019-00062.
CV_Curtis L. Ruegg, Ph.D.; IPR2021-01203.
CV_Hyun-Ho Jung; PGR2019-00062.
CV_Nowell Solish, MD; IPR2021-01203.
CV_Xiaoming Lin; PGR2019-00062.
IPR2021-01203 mailed Jul. 26, 2021, Notice of Filing Date Accorded to Petition and Time for Filing Patent Owner Preliminary Response.
IPR2021-01203 submitted Aug. 30, 2021, Patent Owner's Mandatory Notices Pursuant To 37 C.F.R. § 42.8(a)(2).

(Continued)

*Primary Examiner* — Jennifer E Graser
(74) *Attorney, Agent, or Firm* — CANTOR COLBURN LLP

(57) ABSTRACT

The invention relates to the use of an animal-protein-free botulinum toxin composition to treat a disease, disorder or condition in a patient in need thereof whereby the animal-protein-free botulinum toxin composition exhibits a longer lasting effect in the patient compared to an animal-protein-containing botulinum toxin composition.

19 Claims, 10 Drawing Sheets

(56) References Cited

OTHER PUBLICATIONS

IPR2021-01203 submitted Dec. 6, 2021, Patent Owner's Sur-Reply to Petitioner's Reply to Patent Owner's Preliminary Response.
IPR2021-01203 submitted Jul. 1, 2021, Petition for Inter Partes Review of U.S. Pat. No. 9,480,731 B2.
IPR2021-01203 submitted Jun. 16, 2021, Declaration of Andreas Rummel, Ph.D.
IPR2021-01203 submitted Jun. 16, 2021, Declaration of Curtis Ruegg, Ph.D.
IPR2021-01203 submitted Jun. 16, 2021, Declaration of Sylvia D. Hall-Ellis, Ph.D.
IPR2021-01203 submitted Nov. 18, 2021, Revance Therapeutics, Inc.'S Updated Mandatory Notices.
IPR2021-01203 submitted Nov. 29, 2021, Petitioner's Reply to Patent Owner's Preliminary Response.
IPR2021-01203 submitted Oct. 26, 2021, Patent Owner's Preliminary Response.
IPPR2021-01203 submitted Sep. 15, 2021, Patent Owner's First Updated Mandatory Notices.
IPR2021-01203, submitted Jun. 15, 2021, Declaration of Nowell Jay Solish, M.D., FRCP.
IPR2021-01204 mailed Jul. 26, 2021, Notice of Filing Date Accorded to Petition and Time for Filing Patent Owner Preliminary Response.
IPR2021-01204 submitted Aug. 30, 2021, Patent Owner's Mandatory Notices Pursuant to 37 C.F.R. § 42.8(a)(2).
IPR2021-01204 submitted Dec. 6, 2021, Patent Owner's Sur-Reply to Petitioner's Reply to Patent Owner's Preliminary Response.
IPR2021-01204 submitted Jul. 1, 2021, Petition for Inter Partes Review of U.S. Pat. No. 9,480,731 B2.
IPR2021-01204 submitted Nov. 15, 2019, Petitioner's Updated Mandatory Notices.
IPR2021-01204 submitted Nov. 29, 2021, Petitioner's Reply to Patent Owner's Preliminary Response.
IPR2021-01204 submitted Oct. 26, 2021, Patent Owner's Preliminary Response.
IPR2021-01204 submitted Sep. 15, 2021, Patent Owner's First Updated Mandatory Notices.
PGR2019-00062, Email Comunication References (May 17, 2017-Jan. 15, 2021).
2013 Plastic Surgery Statistics Report, ASPS National Clearinghouse of Plastic Surgery Procedural Statistics, 2013, pp. 1-23.
Ae-Ran Kwon et al., "Activities of Clindamycin, Synercid, Telithromycin, Linezolid, and Mupirocin against Gram-positive Coccal Strains Resistant to Erythromycin in Korea," 2007, pp. 840-843, vol. 30, No. 7.
Alastair Carruthers et al., "Botulinum Toxin," 3rd Edition 2013, pp. 1-50.
Alastair Carruthers et al., "Dose-Ranging Study of Botulinum Toxin Type A in the Treatment of Glabellar Rhytids in Females," Apr. 2005, pp. 1-9, vol. 31, No. 4.
Alastair Carruthers et al., "History of the Cosmetic Use of Botulinum A Exotoxin," Cosmetic Use History of Botulinum Toxin, 1998, pp. 1168-1170, vol. 24.
Alastair Carruthers et al., "Prospective, Double-Blind, Randomized, Parallel-Group, Dose-Ranging Study of Botulinum Toxin Type A in Men with Glabellar Rhytids," Published by BC Decker Inc, 2005, pp. 1297-1303, vol. 31.
Allergan, Botox® Cosmetic (Botulinum Toxin Type A) Purified Neurotoxin Complex, 2002, pp. 1-15.
Andre Ziegler et al., "Interaction of the Protein Transduction Domain of HIV-1 Tat with Heparan Sulfate: Binding Mechanism and Thermodynamic Parameters," Biophysical Journal, Jan. 2004, pp. 254-263, vol. 86.
Andy Pickett, "Consistent Biochemical Data are Essential for Comparability of Botulinum Toxin Type A Products," Correspondence, 2011, pp. 97-99.
Anna Kutschenko et al., "Botulinum Toxin-Induced Focal Paresis in Mice is Unaffected by Muscle Activity," Muscle & Nerve, Dec. 2011, pp. 930-936.

Anthony McCluskey et al., "Statistics IV: Interpreting the results of statistical tests," Continuing Education in Anaesthesia, Critical Care and Pain, 2007, pp. 208-212, vol. 7, No. 6.
Asa Lijegren Sundberg et al. "Relabotulinum toxin—a novel, high purity BoNT-A1 in liquid formulation" Poster, Galderma, 2021, https://www.neurotoxins.org/toxins-2021-virtual/posters/entry/16100/.
Ashwin Parenky et al., "New FDA Draft Guidance on Immunogenicity" The AAPS Journal, Mar. 29, 2014, pp. 499-503, vol. 16, No. 3.
B Rzany et al., "Treatment of glabellar lines with botulinum toxin type A (Speywood Unit): a clinical overview," JEADV, 2010, pp. 1-14, vol. 24.
Bahman Guyuron et al., "Aesthetic Indications for Botulinum Toxin Injection," Plastic and Reconstructive surgery, Apr. 1994, pp. 913-918.
Bahram Mohammadi et al., "Experience with long-term treatment with albumin-supplemented botulinum toxin type A," J Neural Transm, Mar. 25, 2009, pp. 437-441, vol. 116.
Benjamin Ascher et al., "A multicenter, randomized, double-blind, placebo-controlled study of efficacy and safety of 3 doses of botulinum toxin A in the treatment of glabellar lines," J Am Acad Dermatol, Aug. 2004, pp. 223-233, vol. 51, No. 2.
Benjamin Ascher et al., "Liquid Formulation of AbobotulinumtoxinA: A 6-Month, Phase 3, Double-Blind, Randomized, Placebo-Controlled Study of a Single Treatment, Ready-to-Use Toxin for Moderate-to-Severe Glabellar Lines," Cosmetic Medicine, Feb. 14, 2017, pp. 183-191, vol. 38(2).
Berthold Rzany et al., "Recommendations for the Best Possible Use of Botulinum Neurotoxin Type A (Speywood Units) for Aesthetic Applications," Journal of Drugs in Dermatology, 2013, pp. 80-84, vol. 12 (1).
Botox Cosmetic Glabellar Lines, 2012, pp. 1-11.
Botox Cosmetic Lateral Canthal Line, 2013, pp. 1-16.
Botox Label Urinary and Bladder, 2013, pp. 1-36.
Botox prescribing label 2013, pp. 1-16.
Botox Supplemental Label Multiple Conditions, 2011, pp. 1-44.
Botox, 2019, pp. 1-18.
Brittany Meiling, News, https://endpts.com/watch-out-allergan-revances-wrinkle-reducer-beats-botox-in-phili-trials/, Dec. 5, 2017, pp. 1-2.
Cesare Montecucco et al., "Botulinal neurotoxins: revival of an old killer," Opinion in Pharmacology, Apr. 16, 2005, pp. 274-279, vol. 5.
Christopher L. Hankins et al., "Botulinum A Toxin for Glabellar Wrinkles," American Society for Dermatologic Surgery, Elsevier Science, 1998, pp. 1181-1183.
Chuan-Jie Wu et al., "Botulinum toxin type A for the treatment of trigeminal neuralgia: results from a randomized, double-blind, placebo-controlled trial," Cephalalgia, 2012, pp. 443-450.
Company Presentation Dec. 2019, Daring to make a difference, pp. 1-25.
Dalano Hoang, "A Practical Guide to Botulinum Toxin Procedures," Lippincott Williams & Wilkins, a Wolters Kluwer, 2012, pp. 1-7, 26-48, and 198.
Darrell Sleep et al., "Albumin as a versatile platform for drug half-life extension," Biochimica et Biophysica Acta, Apr. 29, 2013, pp. 5526-5534, vol. 1830.
Divakara Kedlaya et al., "Botulinum Toxin," Medscape, Oct. 10, 2019, pp. 1-19, https://emedicine.medscape.com/article/325451.
Doris Hexsel et al., "Field effect of two commercial preparations of botulinum toxin type A: A prospective, double-blind, randomized clinical trial," JAMA Dermatol, Oct. 9, 2013, pp. 1386-1391, vol. 149, No. 12.
Dorothea Sesardic et al., "Alternatives to the LD50 assay for botulinum toxin potency testing: Strategies and progress towards refinement, reduction and replacement," Japanese Society for Alternatives to Animal Experiments, AATEX 14, 2008, pp. 581-585.
Dorothea Sesardic et al., "Refinement and Validation of an Alternative Bioassay for Potency Testing of Therapeutic Botulinum Type A Toxin," Pharmacology & Toxicology, 1996, pp. 283-288, vol. 78.
Dorothea Sesardic, "Is it Possible to Accurately Determine Content of Botulinum Neurotoxin Type A in Drug Products?," Commentary, 2010, pp. 91-92, vol. 10.

(56) References Cited

OTHER PUBLICATIONS

Dorothea Sesardica., "Role for standards in assays of botulinum toxins: international collaborative study of three preparations of botulinum type A toxin," Biologicals, 2003, pp. 265-276, vol. 31.
Edward J. Schantz et al., "Botulinum Toxin: The Story of Its Development for the Treatment of Human Disease," Biology and Medicine, 1997, pp. 317-327, vol. 40, No. 3.
Edward J. Schantz et al., "Properties and Use of Botulinum Toxin and Other Microbial Neurotoxins in Medicine," Microbiological Reviews, 1992, pp. 80-99, vol. 56, No. 1.
Edward J. Schantz et al., "Standardized Assay for Clostridium botulinum Toxins," Journal of The AOAC, 1978, pp. 96-99, vol. 61, No. 1.
Edward T. Maggio, "Polysorbates, peroxides, protein aggregation, and immunogenicity a growing concern," J. Excipients and Food Chem., 2012, pp. 45-53, vol. 3.
Elena Fonfria et al., "The Expanding Therapeutic Utility of Botulinum Neurotoxins," Toxins, May 18, 2018, pp. 1-27.
Emily Ha et al., "Peroxide Formation in Polysorbate 80 and Protein Stability," Journal of Pharmaceutical Sciences, Oct. 2002, pp. 2252-2264, vol. 91, No. 10.
Enrique Garcia-Murray et al., "Safety and Efficacy of RT002, an Injectable Botulinum Toxin Type A, for Treating Glabellar Lines: Results of a Phase 1/2, Open-Label, Sequential Dose-Escalation Study," Dermatologic Surgery, 2015, pp. S47-S55.
FDA Approved Labeling, Apr. 29, 2009, Dysport prescribing label 2009, pp. 1-50.
Gabriele Muti et al., "A Prospective Rater- and Subject-Blinded Study Comparing the Efficacy of IncobotulinumtoxinA and OnabotulinumtoxinA to Treat Crow's Feet: A Clinical Crossover Evaluation," Dermatologic Surgery, 2014, pp. S39-S46.
Galderma Announces Phase 3 Trials for Liquid Neurotoxin, Oct. 19, 2020, pp. 1-2, https://www.medestheticsmag.com/news/news/21198355/galderma-announces-phase-3-trials-for-liquid-neurotoxin.
Gary D. Monheit et al., "Evaluation of QM1114, a Novel Ready-Touse Liquid Botulinum Toxin, in Aesthetic Treatment of Glabellar Lines," 24th World Congress of Dermatology MLAN 2019, Jun. 2019, pp. 1-2.
Gary Monheit et al., "A Randomized, Double-Blind, Placebo-Controlled Study of Botulinum Toxin Type A for the Treatment of Glabellar Lines: Determination of Optimal Dose," Dermatologic Surgery, 2007, pp. S51-S59.
PGR2019-00062, ,Oct. 28, 2020, Second Declaration of Dr. Ash Ramzan.
PGR2019-00062, 2021, Third Declaration of Dr. Ash Ramzan Regarding Patent Owner's Revised Motion to Amend.
PGR2019-00062, Aug. 13, 2021, Patent Owner's Updated Mandatory Notice.
PGR2019-00062, Aug. 16, 2021, Patent Owner's Request for Director Review and, in The Alternative, Panel Rehearing.
PGR2019-00062, Aug. 5, 2020, Declaration of Dr. Ashwani Singh.
PGR2019-00062, Dec. 11, 2020, Declaration of Andrew Martin Pickett, Ph.D., B.Sc.
PGR2019-00062, Dec. 11, 2020, Second Declaration of Dr. Ashwani Singh.
PGR2019-00062, Dec. 23, 2019, Patent Owner's Preliminary Response Under 37 C.F.R. §42.107.
PGR2019-00062, Dec. 23, 2020, Grant of Good Cause Extension.
PGR2019-00062, Dec. 4, 2020, Videotaped Videoconference Deposition of Ash Ramzan, Ph.D.
PGR2019-00062, Dec. 7, 2020, Continued Videotaped Videoconference Deposition of Ash Ramzan, Ph.D.
PGR2019-00062, Corrected Declaration of Charles Russell Middaugh, PhD, 1st, submitted Feb. 19, 2021.
PGR2019-00062, Corrected Declaration of Charles Russell Middaugh, PhD, 2nd, submitted Feb. 19, 2021.
PGR2019-00062, Corrected Declaration of Charles Russell Middaugh, PhD, 3rd, submitted Feb. 19, 2021.
PGR2019-00062, Feb. 10, 2020, Patent Owner's Updated Mandatory Notice Under 37 C.F.R. § 42.8(a)(3).
PGR2019-00062, Feb. 10, 2021, Videoconference Deposition of Ash Ramzan, Ph.D.
PGR2019-00062, Feb. 19, 2021, Third Declaration of Dr. Ashwani Singh.
PGR2019-00062, Galderma, Employment Termination Agreement, 2017.
PGR2019-00062, Hearing Transcript, Jul. 14, 2021.
PGR2019-00062, Jan. 18, 2021, Declaration of Xiaoming Lin in Support of Petitioners' Motion to Disqualify Andrew M. Pickett.
PGR2019-00062 exhibit 1089, Jan. 18, 2021, depositions.
PGR2019-00062, Jan. 19, 2021, Declaration of Joseph A. Mahoney in Support of Petitioners' Motion to Disqualify Dr. Andrew M. Pickett.
PGR2019-00062 exhibit 1094 Jan. 19, 2021, depositions.
PGR2019-00062, Jan. 27, 2020, Declaration Supporting Patent Owner's Motion Opposing Disqualification of its Expert Andrew Martin Pickett, Ph.D., B.Sc.
PGR2019-00062, Jul. 16, 2020, Remote Zoom Audio/Video deposition of Ashramzan, Ph.D.
PGR2019-00062, Jul. 16, 2021, Termination Decision Document (Judgment: Final Written Decision).
PGR2019-00062, Jul. 17, 2020, Remote Zoom Audio/Video deposition of Ashramzan, Ph.D.
PGR2019-00062 exhibit 64, Mar. 18, 2021, Patent Owners' Demonstratives for Hearing.
PGR2019-00062 exhibit 63, Mar. 18, 2021, Petitioners' Demonstratives for Hearing.
PGR2019-00062, Mar. 19, 2020, Decision, Granting Institution of Post-Grant Review 35 U.S.C. § 324 and 37 C.F.R. § 42.208.
PGR2019-00062, Mar. 19, 2020, Scheduling Order.
PGR2019-00062, Mar. 19, 2021, Petitioner's Demonstratives for Final Oral Hearing.
PGR2019-00062, Mar. 8, 2021, vol. III of the videotaped discovery deposition of Ashwani Singh, MD.
PGR2019-00062, Middaugh Adoption, Declaration of Charles Russell Middaugh PhD, 1st, Dec. 11, 2020.
PGR2019-00062, Middaugh Adoption, Declaration of Charles Russell Middaugh PhD, 2nd, Dec. 11, 2020.
PGR2019-00062, Middaugh Adoption, Declaration of Charles Russell Middaugh PhD, 3rd, Dec. 11, 2020.
PGR2019-00062, Nov. 14, 2019, Declaration in Support of Patent Owner's Motion for Pro Hac Vice Admission of Erica Norey Under 37 C.F.R. § 42.10.
PGR2019-00062, Nov. 15, 2019, Declaration in Support of Patent Owner's Motion for Pro Hac Vice Admission of Ha Kung Wong Under 37 C.F.R. § 42.10.
PGR2019-00062, Nov. 18, 2021, Patent Owner's Notice of Appeal.
PGR2019-00062, Nov. 24, 2020, Preliminary Guidance Patent Owner's Motion to Amend.
PGR2019-00062, Oct. 16, 2020, depositions.
PGR2019-00062, Sep. 1, 2019, Declaration of Dr. Ash Ramzan.
PGR2019-00062, Sep. 10, 2020, Petitioners' Notice of Deposition of Dr. Ashwani Singh.
PGR2019-00062, Sep. 17, 2021, Order Denying Request for Director Review.
PGR2019-00062, Sep. 30, 2021, Patent Owner's Unopposed Motion to Withdraw Counsel.
PGR2019-00062, Jun. 2, 2020, Patent Owner's Updated Mandatory Notices Under 37 C.F.R. § 42.8(a)(3).
Gerhard Sattler et al., "Noninferiority of IncobotulinumtoxinA, Free from Complexing Proteins, Compared with Another Botulinum Toxin Type A in the Treatment of Glabellar Frown Lines," Incobotulinumtoxina for Glabellar Lines, Dec. 2010, pp. 2146-2154.
Hongran F. Stone et al., "Characterization of diffusion and duration of action of a new botulinum toxin type A formulation," Toxicon, May 31, 2011, pp. 159-167, vol. 58.
Hyun-Mi Oh et al., "Efficacy and Safety of a New Botulinum Toxin Type A Free of Complexing Proteins," Toxins, Dec. 24, 2015, pp. 1-9, vol. 8, No. 4.

(56) References Cited

OTHER PUBLICATIONS

Inkyung Jung, "Some Facts That You Might be Unaware of About the P-Value," Archives of Plastic Surgery (APS), 2017, pp. 93-94.
Gary Monheit, et al. "Evaluation of QM114, a novel ready-to-use liquid botulinum toxin, in esthetic treatment of glabellar lines," J Am Acad Dermatol, Dec. 2020, p. AB27.
J. A. Coffield et al., "In Vitro Characterization of Botulinum Toxin Types A, C and D Action on Human Tissues: Combined Electrophysiologic, Pharmacologic and Molecular Biologic Approaches1," ASPET Journals, 1997, pp. 1489-1498, vol. 280, No. 3.
J. Alastair Carruthers et al., "A multicenter, double-blind, randomized, placebo-controlled study of the efficacy and safety of botulinum toxin type A in the treatment of glabellar lines," J Am Acad Dermatol, Jun. 2002, pp. 840-849, vol. 46, No. 6.
Jean Carruthers et al., "Injectable DaxibotulinumtoxinA for the Treatment of Glabellar Lines: A Phase 2, Randomized, Dose-Ranging, Double-Blind, Multicenter Comparison With OnabotulinumtoxinA and Placebo," Dermatologic Surgery, 2017, pp. 1321-1331, vol. 43, No. 1.
Jean D. Carruthers et al., "DaxibotulinumtoxinA for Injection for the Treatment of Glabellar Lines: Results from Each of Two Multicenter, Randomized, Double-Blind, Placebo-Controlled, Phase 3 Studies (Sakura 1 and Sakura 2)," Plastic and Reconstructive Surgery, Jan. 2020, pp. 45-58.
Jeffrey S. Dover et al., "Botulinum Toxin in Aesthetic Medicine: Myths and Realities," Dermatologic Surgery, 2018, pp. 249-260, vol. 44.
Joseph A. Mauriello et al., "Use of Botulinum Toxin in the Treatment of One Hundred Patients with Facial Dyskinesias," Botulinum Toxin, Ophthalmology, 1987, pp. 976-979, Vo. 94.
Jun Hyung Kim et al., "Percutaneous Selective Radiofrequency Nerve Ablation for Glabellar Frown Lines," Facial Surgery, Aesthetic Surgery Journal, 2011, pp. 747-755, vol. 31, No. 7.
Jung Eun Kim et al., "The Efficacy and Safety of Liquid-Type Botulinum Toxin Type A for the Management of Moderate to Severe Glabellar Frown Lines," Cosmetic, Management of Glabellar Frown Lines, 2015, pp. 732-741, vol. 135, No. 3.
Jürgen Frevert et al., "Comparison of botulinum neurotoxin type A formulations in Asia," Clinical, Cosmetic and Investigational Dermatology, 2018, pp. 327-331, vol. 11.
Jurgen Frevert, "Content of Botulinum Neurotoxin in Botox/Vistabel, Dysport/Azzalure, and Xeomin/Bocouture," Original Research Article, 2010, pp. 67-73, vol. 10.
Jürgen Frevert, "Pharmaceutical, Biological, and Clinical Properties of Botulinum Neurotoxin Type A Products," Drugs RD, Adis, Jan. 6, 2015, pp. 1-9, vol. 15.
K. R. Aoki et al., "A comparison of the safety margins of botulinum neurotoxin serotypes A, B, and F in mice," Toxicon, 2001, pp. 1815-1820, Vo. 39.
K. Roger Aoki et al., "Preclinical update on Botox® (botulinum toxin type A)-purified neurotoxin complex relative to other botulinum neurotoxin preparations," European Journal of Neurology, 1999, pp. S3-S10, vol. 6.
Karl-Heinz Eisele et al., "Studies on the dissociation of botulinum neurotoxin type A complexes," Toxicon, Dec. 30, 2010, pp. 555-565, vol. 57.
Katarzyna Szymczyk et al., "Adsorption and wetting properties of cationic, anionic and nonionic surfactants in the glass-aqueous solution of surfactant-air system," Materials Chemistry and Physics, May 30, 2015, pp. 166-176, vol. 162.
Kay McLellan et al., "Therapeutic Botulinum Type A Toxin: Factors Affecting Potency," Toxicon, 1996, pp. 975-985, vol. 34, No. 9.
Kim Hyo-jin, "Medytox shares plunge after its flagship botoxproduct loses license," Pulse by Maeil Business Newspaper & mk.co.kr, pp. 1-2, Jun. 18, 2020, https://pulsenews.co.kr/print.php?year=2020&no=624621.
Kine Marita Knudsen Sand, et al., "Unraveling the interaction between FcRn and albumin: opportunities for design of albumin-based therapeutics," Frontiers in Immunology, Immunotherapies and Vaccines, Jan. 26, 2015, pp. 1-21, vol. 5, Article 682.
Kiyonori Harii et al., "A Double-Blind, Randomized, Placebo-Controlled, Two-Dose Comparative Study of Botulinum Toxin Type A for Treating Glabellar Lines in Japanese Subjects," Aesth Plast Surg, Jul. 29, 2008, pp. 724-730, vol. 32.
Ko Jun-Tae, "An uncertain future for Medytox," Oct. 26, 2020, pp. 1-3, https://koreajoongangdaily.joins.com/2020/04/20/industry/NEWS-IN-FOCUS-An-uncertain-future-for-Medytox/3076276.html.
Koenraad De Boulle et al., "Treating glabellar lines with botulinum toxin type A-hemagglutinin complex: A review of the science, the clinical data, and patient satisfaction," Clinical Interventions in Aging, 2010, pp. 101-118, vol. 5.
Kwangkook Lee et al., "Structure of a Bimodular Botulinum Neurotoxin Complex Provides Insights into its Oral Toxicity," PLOS Pathogens, Oct. 2013, pp. 1-13 (e1003690), vol. 9, Issue 10.
L. Bruce Pearce et al., "The Median Paralysis Unit:A More Pharmacologically Relevant Unit of Biologic Activity for Botulinum Toxin," Toxicon, 1995, pp. 217-227, vol. 33, No. 2.
Lars Hovgaard et al., "2nd Edition, Pharmaceutical Formulation Development of Peptides and Proteins," Book, pp. 297-322.
Lee Han-soo, "Medytox launches 3rd BTX product," Korea Biomedical Review, Mar. 20, 2019, pp. 1-2.
Leslie Winter et al., "Botulinum toxin type-A in the treatment of glabellar lines," Clinical, Cosmetic and Investigational Dermatology, 2010, pp. 1-4, vol. 3.
Letter "In the Matter of Certain Botulinum Toxin Products, Processes for Manufacturing or Relating to Same and Certain Products Containing Same; Inv. No. 337-TA -," Jan. 25, 2019, pp. 1-76.
Letter of 2009, Department of Health & Human Services, pp. 1-5.
Lim Jeonguyeo, "Medytox's Coretox at risk of losing license," issued Oct. 20, 2020, www01.koreaherald.com/common/newsprint.php?ud=20201020000892.
Lim Jeong-yeo, "Drug Ministry Revokes Meditoxin License," Jun. 18, 2020, pp. 1-3, http://www.koreaherald.com/common/newsprint.php?ud=20200618000755.
Malgorzata Field et al., "AbobotulinumtoxinA (Dysport®), OnabotulinumtoxinA (Botox®), and IncobotulinumtoxinA (Xeomin®) Neurotoxin Content and Potential Implications for Duration of Response in Patients," toxins, Dec. 13, 2018, pp. 1-14, vol. 10, No. 535.
Mark S. Nestor et al., "The mechanisms of action and use of botulinum neurotoxin type A in aesthetics: Key Clinical Postulates II," J Cosmet Dermatol, 2020, pp. 2785-2804, vol. 19.
Markus Naumann et al., "Immunogenicity of botulinum toxins," J Neural Transm, Sep. 25, 2012, pp. 275-290, vol. 120.
Medication Guide, "Botox® Cosmetic (Boe-tox) (onabotulinumtoxinA) for injection, for intramuscular, Intradetrusor, or intradermal use" 2021, pp. 1-4.
Medytox History, Thursday, Jan. 21, 2021, pp. 1-3, http://www.medytox.com/page/history_en?site_id=en.
Medytox ITC Final Initial Determination, Inv. No. 337-TA-1145, Aug. 6, 2020, pp. 1-273.
Medytox Website, "Press Release By Medytox on the Disclosure of Full Text of U.S. ITC Final Rulling," Jan. 20, 2021, http://www.medytox.com/.
Michael C. Goodnough et al., "Stabilization of Botulinum Toxin Type A during Lyophilization," Applied and Environmental Microbiology, Oct. 1992, pp. 3426-3428.
Mitchell F. Brin et al., "Botulinum toxin type A products are not interchangeable: a review of the evidence," Biologics: Targets and Therapy, 2014, pp. 227-241, vol. 4, No. 8.
Mosby's Dictionary 8th Edition (Mosby 'S Dictionary of Medicine, Nursing & Health Professions), ISBN: 978-0-323-04937-5, published 2009, pp. 1063 and 1157.
Naveed Panjwani et al., "Biochemical, functional and potency characteristics of type A botulinum toxin in clinical use," The Botulinum J., 2008, pp. 153-166, vol. 1, No. 1.
Paola L. Carvajal Monroy et al., "Isolation and Characterization of Satellite Cells from Rat Head Branchiomeric Muscles," Journal of Visualized Experiments, Jul. 20, 2015, pp. 1-11, vol. 101.
Paolo Persichetti et al., "Inability of Speculation to Explain Dose Effect Differences Between Botulinum Toxin Products," Arch Facial Plast Surg, 2012, pp. 467-468, vol. 14, No. 6.

(56) References Cited

OTHER PUBLICATIONS

Pharmaceutical Online, "FDA Gives Update on Botulinum Toxin Safety Warnings; Established Names of Drugs Changed," Aug. 4, 2009.
Physicians' Desk reference, Botox PDR, 2003, pp. 547-552.
D. Dressler, "Five-year experience with incobotulinumtoxinA (Xeomin(®) ): the first botulinum toxin drug free of complexing proteins," European Journal of Neurology, Mar. 2012, pp. 385-389, vol. 19, No. 3.
Extended European Search Report dated Jun. 2, 2021 of EP Divisional Patent Application No. 20209237.5.
IPR2021-01203, Jan. 19, 2022, Decision, Denying Institution of Inter Partes Review 35 U.S.C. § 314, pp. 1-17.
IPR2021-01204, Jan. 19, 2022, Decision Denying Institution of Inter Partes Review 35 U.S.C. § 314, pp. 1-20.
PGR2019-00062 Patent Owner's Exhibit List 4 (2001-2100) Jan. 27, 2021.
PGR2019-00062 Patent Owner's Exhibit List 5 (2001-2100) Feb. 19, 2021.
PGR2019-00062 Patent Owner's Exhibit List No. 1 (2001-2002) Nov. 15, 2019.
PGR2019-00062 Patent Owner's Exhibit List No. 2 (2001-2023) Aug. 5, 2020.
PGR2019-00062 Patent Owner's Exhibit List No. 3 (2001-2100), Dec. 11, 2020.
PGR2019-00062, Apr. 29, 2020, Amended Scheduling Order.
PGR2019-00062, Aug. 16, 2021, Notice of Request for Director Review—Ex. 3100.
PGR2019-00062, Aug. 5, 2020, Motion to Amend Under 37 C.F.R. §42.221.
PGR2019-00062, Dec. 11, 2020, Patent Owner's Revised Motion to Amend.
PGR2019-00062, Dec. 23, 2020, Extending One-Year Pendency for Good Cause 35 U.S.C. § 326(a)(11); 37 C. F.R. § 42.200(c).
PGR2019-00062, Dec. 23, 2020, Order—Revised Scheduling Order.
PGR2019-00062, Feb. 10, 2020, Patent Owner's Motion to Withdraw Pro Hac Vice Motion of Erica Norey.
PGR2019-00062, Feb. 11, 2021, Order Setting Oral Argument 37 C.F.R. § 42.70.
PGR2019-00062, Feb. 11, 2021, Granting Patent Owner's Motion to Disqualify Andrew M. Pickett as Patent Owner's Expert Witness 37 C.F.R. §§ 42.5, 42.20.
PGR2019-00062, Feb. 16, 2021, Order—Further Revised Scheduling Order.
PGR2019-00062, Feb. 19, 2021, Patent Owner's Reply in Support of Patent Owner's Revised Motion to Amend.
PGR2019-00062, Feb. 24, 2021, Conduct of the Proceeding 37 C.F.R. § 42.5.
PGR2019-00062, Feb. 24, 2021, Corrected Patent Owner's Reply in Support of Patent Owner's Revised Motion to Amend.
PGR2019-00062, Feb. 5, 2020, Patent Owner's Notice of Deposition of Dr. Ash Ramzan.
PGR2019-00062, Feb. 5, 2021, Patent Owner's Objections to Evidence.
PGR2019-00062, Feb. 5, 2021, Patent Owners' Request for Oral Argument Pursuant to 37 C. F.R. § 42.70(a).
PGR2019-00062, Feb. 5, 2021, Petitioners' Request for Oral Argument.
PGR2019-00062, Jan. 18, 2021, Petitioners' Notice of Deposition of Dr. Andrew M. Pickett.
PGR2019-00062, Jan. 18, 2021, Petitioners' Notice of Deposition of Dr. Ashwani Singh.
PGR2019-00062, Jan. 19, 2020, Petitioners' Motion to Seal and for Entry of a Protective Order Pursuant to 37 C.F.R. § 42.54.
PGR2019-00062, Jan. 19, 2021, Petitioner's Motion to Disqualify Andrew M. Pickett.
PGR2019-00062, Jan. 22, 2021, Petitioner's Opposition to Patent Owner's Revised Motion to Amend.
PGR2019-00062, Jan. 27, 2021, Motion to Seal Patent Owners' Opposition to Petitioner's Motion to Disqualify Andrew M. Pickett and Related Exhibits.
PGR2019-00062, Jan. 27, 2021, Patent Owner's Opposition to Petitioner's Motion to Disqualify Dr. Pickett [Redacted].
PGR2019-00062, Jul. 13, 2020, Patent Owner's Amended Notice of Deposition of Dr. Ashramzan.
PGR2019-00062, Jun. 26, 2020, Patent Owner's Notice of Deposition of Dr. Ash Ramzan.
PGR2019-00062, Jun. 5, 2020, Notice of Stipulation.
PGR2019-00062, Mar. 10, 2021, Notice of Stipulation.
PGR2019-00062, Mar. 12, 2021, Petitioners' Sur-Reply in Opposition Topatent Owner's Revised Motion to Amend.
PGR2019-00062, Mar. 19, 2021, Patent Owner's Demonstratives for Final Oral Hearing (2074).
PGR2019-00062, Mar. 3, 2021, Petitioners' Notice of Deposition of Dr. Ashwani Singh.
PGR2019-00062, Mar. 3, 2021, Petitioners' Notice of Deposition of Charles R. Middaugh, Ph.D.
PGR2019-00062, Mar. 5, 2021, Middaugh Deposition Transcript.
PGR2019-00062, Nov. 15, 2019, Patent Owner's Motion for Pro Hac Vice Admission of Ha Kung Wong Under 37 C.F.R § 42.10.
PGR2019-00062, Nov. 15, 2019, Patent Owner's Mandatory NoticeS—37 C.F.R. § 42.8.
PGR2019-00062, Nov. 15, 2019, Patent Owner's Motion for Pro Hac Vice Admission of Erica Norey Under 37 C.F.R § 42.10.
PGR2019-00062, Nov. 4, 2020, Patent Owner's Objections to Evidence.
PGR2019-00062, Oct. 18, 2019, Petitioners' Updated Mandatory Notice Regarding Real Parties-In-Interest.
PGR2019-00062, Oct. 20, 2020, Order Conduct of the Proceeding 37 C.F.R. § 42.5.
PGR2019-00062, Oct. 28, 2020, Petitioners' Opposition to Patent Owner's Noncontingent Motion to Amend Claims of U.S. Pat. No. 10,143,728.
PGR2019-00062, Sep. 25, 2019, Notice of Filing Date Accorded to Petition and Time for Filing Patent Owner Preliminary Response.
PGR2019-00062, Sep. 4, 2019, Petition for Post-Grant Review of U.S. Pat. No. 10, 143,728.
PGR2019-00062, Dec. 2, 2020, Patent Owner's Notice of Deposition of Dr. Ash Ramzan.
PGR2019-00062, Jan. 13, 2021, Conduct of the Proceeding 37 C.F.R. sec 42.5.
Priya Ranganathan et al., "Common pitfalls in statistical analysis: Clinical versus statistical significance," Journal of the Royal Society of Medicine, Nov. 1994, p. 719, vol. 87.
R. Glogau et al., Journal of Drugs in Dermatology: JDD, Jan. 2012, pp. 38-45, vol. 11, Issue 1.
Regina Nuzzo, "Statistical Errors," Nature, Feb. 13, 2014, pp. 150-152 and 131-132, vol. 506.
Revance Press Release Details, "Revance Reports Results for RT001 Topical Phase 3 Trial for Lateral Canthal Lines" , Jun. 13, 2016, pp. 1-5, https://investors.revance.com/news-releases/news-release-details/revance-reports-results-rt001-topical-phase-3-trial-lateral.
Richard G. Wenzel, "Pharmacology of botulinum neurotoxin serotype A," Symposium Pharmacology, Am J Health-Syst Pharm-, Nov. 15, 2004, vol. 61, pp. S5-S10.
Richard Glogau et al., "OnabotulinumtoxinA: A Meta-Analysis of Duration of Effect in the Treatment of Glabellar Lines," Dermatologic Surgery, Nov. 2012, pp. 1794-1803, vol. 38, No. 11.
Rodney L. Levine et al., "Methionine residues as endogenous antioxidants in proteins," Clinical Neurophysiology, Dec. 13, 2012, pp. 999-1004, vol. 124.
Ron S. Broide et al., "The rat Digit Abduction Score (DAS) assay: A physiological model for assessing botulinum neurotoxin-induced skeletal muscle paralysis," Toxicon, May 23, 2013, pp. 18-24, vol. 71.
Ronald A. Rader, "Nomenclature of New Biosimilars Will be Highly Controversial," BioProcess International, Jun. 2011, pp. 28-32.

(56) References Cited

OTHER PUBLICATIONS

Ronald Moy et al., "Long-term Safety and Efficacy of a New Botulinum Toxin Type A in Treating Glabellar Lines," Arch Facial Plast Surg. 2009, pp. 77-83.
Rupp et al., "OnabotulinumtoxinA Displays Greater Biological Activity Compared to IncobotulinumtoxinA, Demonstrating Non-Interchangeability in Both In Vitro and In Vivo Assays" Toxins, Jun. 13, 2020, pp. 1-15, vol. 12, No. 393.
Sarah-Jane Duquemin et al., "The effect of sodium lauryl sulphate, cetrimide and polysorbate 20 surfactants on complex coacervate volume and droplet size," J. Pharm. Pharmacol, 1985, pp. 698-702, vol. 37.
Seongsung Kwak et al., "Comparative Pharmacodynamics Study of 3 Different Botulinum Toxin Type A Preparations in Mice," Comparative Bont/A Pharmacodynamics, 2020, pp. 1-7.
Sheng Chen, "Clinical Uses of Botulinum Neurotoxins: Current Indications, Limitations and Future Developments," toxins, Oct. 19, 2012, pp. 913-939, vol. 4.
Sohn Jiuyoung, "Allergan to begin phase 3 trials of Medytox's 'Innotox' in US, Canada this week," Oct. 29, 2018 16:16, pp. 1-2, www.koreaherald.com/common/newsprint.php?ud=20181029000729.
Song Kyoung-Son, "Medytox loses sales licenses for three most popular products," Oct. 26, 2020, pp. 1-2, https://koreajoongangdaily.joins.com/2020/06/18/business/industry/Medytox-Meditoxine-botox/20200618195600274.html.
Souphiyeh Samizadeh et al., "Botulinum neurotoxin formulations: overcoming the confusion," Clinical, Cosmetic and Investigational Dermatology, 2018, pp. 273-287, vol. 11.
Statement on a Nonproprietary Name Adopted by The USAN Council, USAN (AbobotulinumtoxinA), p. 1; PGR2019-00062, Exhibit 2059.
Stefano Schiaffino et al., "Fiber Types in Mammalian Skeletal Muscles," Physiological reviews, 2011, pp. 1447-1531, vol. 91.
Stephen I. Toth et al., "Extreme Sensitivity of Botulinum Neurotoxin Domains Towards Mild Agitation," Journal of Pharmaceutical Sciences, Feb. 18, 2009, pp. 3302-3311, vol. 98, No. 9.
Steven Fagien et al., "Facial rejuvenation with botulinum neurotoxin: An anatomical and experiential perspective," Journal of Cosmetic and Laser Therapy, 2007, pp. 23-31, vol. 9.
Sumit Goswami et al., "Developments and Challenges for mAb-Based Therapeutics," Antibodies, Aug. 16, 2013, pp. 452-500, vol. 2.
Talia Y. Moore et al., "Vertical leaping mechanics of the Lesser Egyptian Jerboa reveal specialization for maneuverability rather than elastic energy storage," Frontiers in Zoology, 2017, pp. 1-12.
Tania Marur et al., "Facial anatomy," Clinics in Dermatology, 2014, pp. 14-23, vol. 32.
Theresa A.N. Ekong et al., "Immunological detection of Clostridium botulinum toxin type A in therapeutic preparations," Journal of Immunological Methods, 1995, pp. 181-191, vol. 180.
Thomas J. Walker et al., "Comparison and Overview of Currently Available Neurotoxins" J Clin Aesthet Dermatol, Feb. 2014, pp. 1-9, vol. 7, No. 2.
Thomas Rappl et al., "Onset and duration of effect of incobotulinumtoxinA, onabotulinumtoxinA, and abobotulinumtoxinA in the treatment of glabellar frown lines: a randomized, double-blind study," Clinical, Cosmetic and Investigational Dermatology, 2013, pp. 211-219, vol. 6.
Timothy Corcoran Flynn, "Botulinum Toxin, Examining Duration of Effect in Facial Aesthetic Applications," Am J Clin Dermatol, 2010, pp. 183-199, vol. 11, No. 3.
U.S. National Libray of Medicine, Clinical Trials Result (Clinicaltrials.gov), Jan. 4, 2021, pp. 1-4.
Vince Bertucci et al., "DaxibotulinumtoxinA for Injection has a prolonged duration of response in the treatment of glabellar lines: Pooled data from two multicenter, randomized, double-blind, placebo-controlled, phase 3 studies (Sakura 1 andSakura 2)," J Am Acad Dermatol, Nov. 29, 2019, pp. 838-845, vol. 82, No. 4.
Wan Long Zhu et al., "Antimicrobial and Cytolytic Activities and Plausible Mode of Bactericidal Action of the Cell Penetrating Peptide Penetratin and its Lys-linked Two-Stranded Peptide," Journal compilation, Chem Biol Drug Des, Dec. 16, 2008, pp. 209-215, vol. 73.
Welf Prager et al., "Differential characteristics of incobotulinumtoxinA and its use in the management of glabellar frown ines," Clinical Pharmacology: Advances and Applications, 2013, pp. 39-52, vol. 5.
World Medical Association Declaration of Helsinki, Oct. 1996, pp. 1-3.
Xeomin prescribing label 2011, pp. 1-13.
Xeomin prescribing information for cervical dystonia and blepharospasm, pp. 1-11, 2010.
Xeomin prescribing information for cervical dystonia, blepharospasm, and glabellar lines, pp. 1-17, 2010.
Yan Wu et al., "Botulinum Toxin Type A for the Treatment of Glabellar Lines in Chinese: A Double-Blind, Randomized, Placebo-Controlled Study," Dermatol Surg, 2010, pp. 102-108, vol. 36.
Clinical Trials Result, pp. 1-4, Jan. 4, 2021.
Dysport Label Cervical Dystonia and Glabellar Lines Apr. 29, 2009, pp. 1-50.
FDA Gives Update on Botulinum Toxin Safety Warnings; Established Names of Drugs Changed, Aug. 4, 2009.
Sarah-Jane Duquemin et al., "The effect of sodium lauryl sulphate, cetrimide and polysorbate 20 surfactants on complex coacervate vol. and droplet size," J. Pharm. Pharmacol, 1985, pp. 698-702, vol. 37.
Song Kyoung-Son, "Medytox loses sales licenses for three most popular products," Jun. 18, 2020, pp. 1-2, https://koreajoongangdaily.joins.com/2020/06/18/business/industry/Medytox-Meditoxine-botox/20200618195600274.html.
Welf Prager et al., "Differential characteristics of incobotulinumtoxinA and its use in the management of glabellar frown lines," Clinical Pharmacology: Advances and Applications, 2013, pp. 39-52, vol. 5.
Xeomin, pp. 1-11, 2010.
Xeomin, pp. 1-17, 2010.

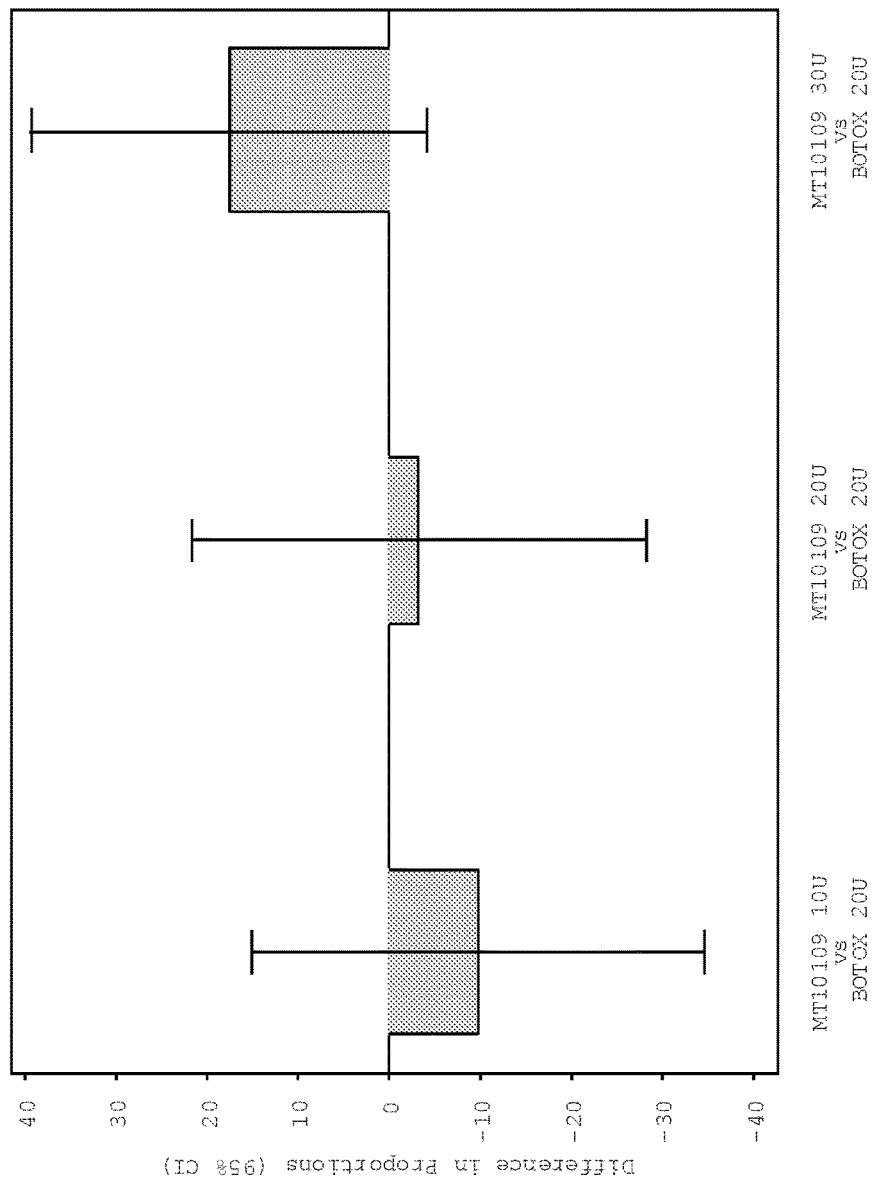

Figure 5

Abbreviations: CI=confidence interval; vs=versus.
Note: A responder was defined as having a glabellar line severity rating of none (0) or mild (1) at the corresponding post-baseline visit. The analysis was on imputed data using multiple imputation methodology. A Mantel-Haenszel chi-square test was used to compare treatments 2 by 2 and estimate the difference between the two treatments.

LONG LASTING EFFECT OF NEW BOTULINUM TOXIN FORMULATIONS

CROSS REFERENCE TO RELATED APPLICATIONS

This application is a continuation of U.S. patent application Ser. No. 17/011,824, filed Sep. 3, 2020, which is a continuation of U.S. patent application Ser. No. 16/207,387, filed Dec. 3, 2018, which is a divisional of U.S. patent application Ser. No. 15/336,119, filed Oct. 27, 2016, now U.S. Pat. No. 10,143,728, issued Dec. 4, 2018, which is a continuation of U.S. patent application Ser. No. 14/567,289, filed Dec. 11, 2014, now U.S. Pat. No. 9,480,731, issued Nov. 1, 2016, which claims the benefit of U.S. Provisional Application Ser. No. 61/915,476, filed Dec. 12, 2013, all hereby incorporated entirely by reference.

BACKGROUND OF THE INVENTION

Pioneered in the mid-late 1980s, chemical denervation of the corrugator and/or procerus muscles with botulinum toxin A (BoNT/A) met many of the criteria of an ideal cosmetic technique for the treatment of glabellar frown lines. When carried out by experienced personnel, BoNT/A injection rapidly and reversibly ameliorates or even eliminates glabellar lines, with virtually no significant adverse effect (Becker-Wegerich P, et al., Clin Exp Dermatol, 2001 October; 26(7):619-30; Letessier S., J Dermatol Treat, 1999; 10(1):31-6 and Alam M, et al., Arch Dermatol, 2002 September; 138(9):1180-5).

In 2002, a decade after the first published report on the use of BoNT/A in the treatment of glabellar frown lines (Carruthers J D A, et al. J Dermatol Surg Oncol, 1992 January; 18(1):17-21) the acknowledged efficacy and tolerability of BoNT/A's effect on glabellar lines was finally confirmed in two identical, large, multicenter, placebo controlled trials (Carruthers J A, et al., J Am Acad Dermatol, 2002 June; 46(6):840-9 and Carruthers J, et al., Journal of Plastic and Reconstructive Surgery 2003). Since then, BoNT/A has been used widely in a variety of manners to temporarily treat glabellar lines and other hyperfunctional facial lines, including horizontal forehead lines ('thinker's wrinkles') and lateral orbital lines ('crow's feet').

Currently commercially available BoNT/A all contain animal proteins such as albumin. Further commercially available BoNT/A compositions such as BOTOX® have a duration of effect of approximately 3 months for treating conditions such as crow's feet lines or glabellar lines.

Accordingly, there is a need in the art for a new type of BoNT composition that is effective and safe with a duration effect longer than commercially available BoNT compositions (e.g. BOTOX®, DYSPORT®, or XEOMIN®). The present invention fulfills this need.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3, comprising

FIG. 4, comprising

FIG. 5 is a graph demonstrating the difference in proportion of responders as indicated by investigator assessment rating of glabellar line severity at maximum frown at day 30 for various dosages of lyophilized MT10109 (10 U, 20 U, and 30 U) compared to 20 U Botox® (full analysis set). Abbreviations. CI=confidence interval; vs=versus. A responder was defined as having a glabellar line severity rating of none (0) or mile (1) at the corresponding post-baseline visit. The analysis was on inputted data using multiple imputation methodology. A Mantel-Haenszel chi-square test was used to compare treatments 2 by 2 and estimate the differences between the two treatments.

DETAILED DESCRIPTION

Figure 1:
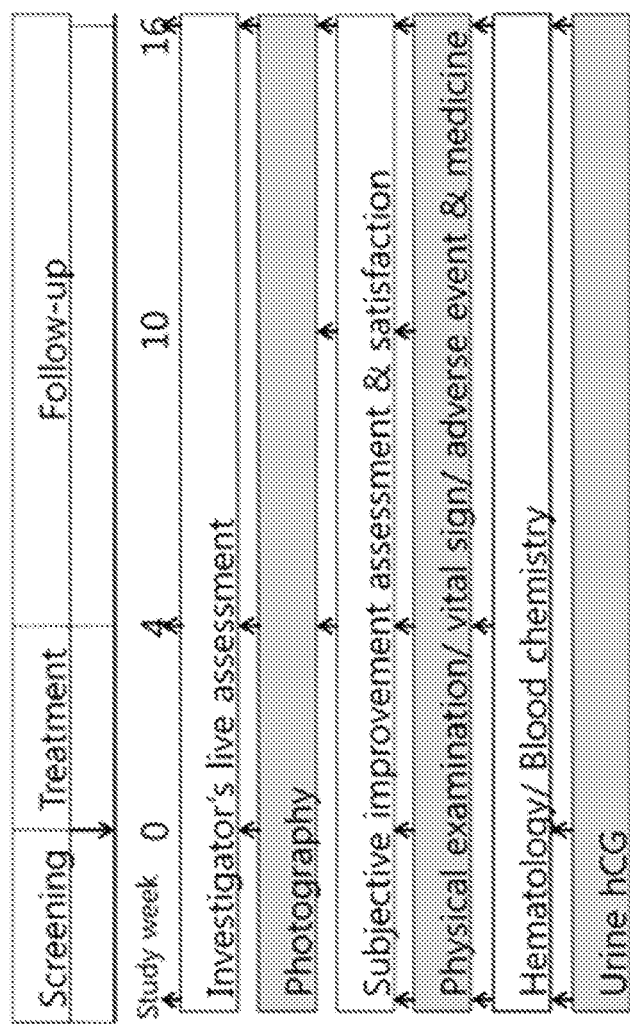
FIG. 1 is an image showing the study design and schedule of assessments.

The invention relates to the use of an animal-protein-free botulinum toxin composition to treat a disease, disorder or condition in a patient in need thereof whereby the animal-protein-free botulinum toxin composition exhibits a longer lasting effect in the patient compared to an animal-protein-containing botulinum toxin composition.

In at least one embodiment, the animal-protein-free botulinum toxin composition is formulated in a liquid form. In certain embodiments the liquid formulation of an animal-protein-free botulinum toxin composition is the formulation disclosed in US 20100291136, which is incorporated herein by reference in its entirety. In certain embodiments, the liquid formulation of an animal-protein-free botulinum toxin composition allows for the activity of botulinum toxin to be stably maintained under a refrigerated or high temperature condition with the use of neither animal-derived protein, such as albumin or gelatin, as a stabilizer for botulinum toxin nor polar or acidic amino acids such as glutamine, glutamic acid, asparagine or aspartic acid.

In at least one embodiment, the animal-protein-free botulinum toxin composition is formulated in a lyophilized form. In certain embodiments the lyophilized preparation of an animal-protein-free botulinum toxin composition is the formulation disclosed in PCT/KR2012/002418, which is incorporated herein by reference in its entirety. In certain embodiments, the lyophilized formulation of an animal-protein-free botulinum toxin composition allows for maintaining botulinum toxin activity and achieving remarkably superior long-term stability even under high-temperature conditions which might occur during storage, transportation, or use of botulinum toxin.

In certain embodiments, the efficacy of the animal-protein-free botulinum toxin composition (e.g., a liquid formulation or a lyophilized form) persists longer in the patient compared to an animal-protein-containing botulinum toxin composition. In certain embodiments, the administration of the animal-protein-free botulinum toxin composition (e.g., a liquid formulation or a lyophilized form) allows for larger interval time between administrations of the botulinum toxin composition compared to the interval time when using an animal-protein-containing botulinum toxin administered at the same or comparable dose and at the same or comparable sites.

In certain embodiments, the invention provides a treatment regimen that includes using an animal-protein-free botulinum toxin composition wherein the botulinum toxin composition is administered to a patient in need thereof at a lower dose compared to the dose used with an animal-protein-containing botulinum toxin composition.

In certain embodiments, the invention provides a treatment regimen that includes using an animal-protein-free botulinum toxin composition wherein the botulinum toxin composition is administered to a patient in need thereof at a greater time interval between administrations compared to the time interval used with an animal-protein-containing botulinum toxin composition (e.g. commercially available botulinum toxin type A includes BOTOX®, DYSPORT®, and XEOMIN®; commercially available botulinum toxin type B includes MyoBloc®).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About," as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "animal-protein-free botulinum toxin composition" refers to a botulinum toxin composition that does not contain blood derived, blood pooled or other animal derived products (e.g. does not contain albumin). In certain embodiments, the animal-protein-free botulinum toxin composition is free of human serum albumin or recombinant human albumin.

As used herein, the term "animal-protein-containing botulinum toxin composition" refers to a botulinum toxin composition that contains a blood derived, blood pooled or other animal derived product (e.g. contains albumin). In certain embodiments, animal-protein-containing botulinum toxin composition contains human serum albumin or recombinant human albumin.

"Botulinum toxin" means a botulinum neurotoxin as either pure toxin or complex, native, recombinant, or modified, and includes botulinum toxin type A, type B, type $C_1$, type D, type E, type F, and type G. As used herein, this term excludes non-neurotoxins, such as the cytotoxic botulinum toxins $C_2$ and $C_3$.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "composition" or "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect ($E_{max}$) achieved within an assay.

"Local administration" means administration of a pharmaceutical agent to or to the vicinity of a muscle or a subdermal location in a patient by a non-systemic route. Thus, local administration excludes systemic routes of administration, such as intravenous or oral administration.

"Long lasting" or "longer lasting" or "greater duration" refers to the longer duration of efficacy of an animal-protein-free botulinum toxin composition when compared to an animal-protein-containing botulinum toxin composition that is dosed at the same or comparable amount and administered in the same manner (e.g. by injection) to the same or comparable location(s).

"Peripheral administration" means administration to a location away from a symptomatic location, as opposed to a local administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

A "therapeutic" treatment is a treatment administered to a subject who exhibits signs or symptoms of pathology, for the purpose of diminishing or eliminating those signs or symptoms.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based on the discovery that an animal-protein-free botulinum toxin composition exhibited an improved outcome in a recipient patient compared to an otherwise identical patient receiving an animal-protein-containing botulinum toxin composition when the patient was evaluated 16 weeks after the administration of the botulinum toxin composition. That is, the animal-protein-free botulinum toxin composition exhibits a longer lasting effectiveness compared to an animal-protein-containing botulinum toxin composition.

Liquid Animal-Protein-Free Formulation

Compositions useful in the invention include an animal-protein-free botulinum toxin composition. In certain embodiments, the animal-protein-free botulinum toxin composition is in a liquid formulation.

In certain embodiments, the liquid pharmaceutical composition used in the present invention comprises botulinum toxin, polysorbate 20, and methionine.

In certain embodiments, the liquid pharmaceutical composition used in the present invention comprises botulinum toxin, polysorbate 20, methionine and isoleucine.

In certain embodiments, the liquid pharmaceutical composition comprises a botulinum toxin, polysorbate 20 and methionine and optionally isoleucine.

With the employment of polysorbate 20, methionine and optionally isoleucine, instead of an animal-derived protein such as albumin or gelatin, as stabilizers for botulinum toxin, the liquid pharmaceutical composition used in the present invention excludes the potential risk of infecting the recipient with serum-derived pathogens or microorganisms and is thus safe for ingestion into the body. In addition, the use of the stabilizers polysorbate 20, methionine and optionally isoleucine allows for higher stability to botulinum toxin composition at around 25° C. to about 37° C. Thus, in terms of the storage stability of botulinum toxin composition at 25° C. to about 37° C., the liquid pharmaceutical composition is very useful for storing botulinum toxin composition under an emergency condition such as an environment without maintaining low temperature, thus being superior to conventional liquid pharmaceutical compositions employing either detergents or amino acids.

In certain embodiments, the methionine is present in an amount of about 0.5 to 100 μmol per 100 units of botulinum toxin, and preferably ranges in concentration from about 0.5 to 100 mM and more preferably from about 25 to about 75 mM. In another embodiment, the methionine ranges in concentration from about 0.5 mM to about 100 mM.

A methionine content less than 0.5 μmol per 100 units of botulinum toxin cannot guarantee the stabilization of the botulinum toxin to a desirable level upon long-term storage at room temperature. On the other hand, when methionine is used in an amount exceeding 100 μmol per 100 units of botulinum toxin, the excess increment may not promise an additional stabilization effect in addition to incurring an economic disadvantage. In the liquid pharmaceutical composition used in the present invention, methionine properly ranges in concentration from 0.5 to 100 mM when the botulinum toxin has a concentration of 100 units/mL. Its proper concentration is adjusted to about 25 mM to about 75 mM in consideration of the concentration range of polysorbate 20. When the concentration of methionine is below 25 mM in the liquid pharmaceutical composition used in the present invention, its long-term stabilization effect on botulinum toxin at room temperature does not reach the desirable level, which is obtainable in the proper concentration range of botulinum toxin. On the other hand, a methionine concentration exceeding 75 mM does not provide any additional effect.

In certain embodiments, polysorbate 20 is present in an amount of 0.01 to 50 mg per 100 units of botulinum toxin and preferably ranges in concentration from 0.01 to 50 mg/mL and more preferably form 0.1 to 2.5 mg/mL.

Polysorbates are a class of emulsifiers used in some pharmaceuticals and in food preparation. They are often used in cosmetics to dissolve essential oils into water-based (oil-in-water) products. There are many kinds of polysorbates that are classified by a number referring to the total number of oxyethylene groups, such as polysorbate 20, 40, 60 and 80. In certain embodiments, the liquid pharmaceutical composition used in the present invention employs polysorbate 20 (commercially available as brand name Tween 20) as a stabilizer for botulinum toxin.

If the liquid pharmaceutical composition used in certain embodiments of the present invention contains polysorbate 20 in an amount less than 0.01 mg per 100 units of botulinum toxin, its long-term stabilization effect on botulinum toxin at room temperature does not reach a desirable level. On the other hand, a polysorbate 20 concentration exceeding 50 mg/mL does not provide any additional effect in addition to incurring an economic disadvantage. At a concentration of 100 units/mL of botulinum toxin in the liquid pharmaceutical composition used in certain embodiments of the present invention, polysorbate 20 is properly present in an amount of about 0.01 mg/mL to about 50 mg/mL and preferably in an amount of about 0.1 mg/mL to about 2.5 mg/mL when the methionine concentration is taken into consideration. When the concentration of polysorbate 20 in the liquid pharmaceutical composition used in certain embodiments of the present invention is less than 0.1 mg/mL, its long-term stabilization effect on botulinum toxin at room temperature does not reach a desired level, which is obtainable by the target concentration of polysorbate 20. On the other hand, a polysorbate 20 concentration exceeding 2.5 mg/mL does not provide any additional effect.

The botulinum toxin, a constituent of the liquid pharmaceutical composition used in certain embodiments of the present invention, may be one selected from among serotypes A, B, C, D, E, F and G. The term botulinum toxin is a generic term embracing the family of toxins produced by the anaerobic bacterium *Clostridium botulinum* and, to date, seven immunologically distinct neurotoxins serotypes have been identified. These have been given the designations A, B, C, D, E, F and G, which differ one from the other in their effects on target animals, and paralysis extent and duration. All serotypes of botulinum toxin are known to act as a neurotoxin by inhibiting the neurotransmitter acetylcholine at neuromuscular junctions.

The botulinum toxin of the liquid pharmaceutical composition used in certain embodiments of the present invention may be in a non-complex form or in a complex form with another protein. Botulinum toxin serotype A, B, C, D, E, F or G alone, synthesized by *Clostridium botulinum*, itself has a molecular weight of approximately 150 kDa. When expressed in *Clostridium botulinum*, the botulinum toxin forms various complexes with hemagglutinin proteins and non-hemagglutinin proteins which aid and protect the activity thereof. Naturally occurring botulinum type A complexes have a molecular weight of approximately 900 kDa, 500 kDa or 300 kDa. Molecular weights are measured to be approximately 500 kDa for botulinum toxin type B complexes and type C complexes, approximately 300 kDa or 500 kDa for type D complexes, and approximately 300 kDa for type E and type F complexes.

In certain embodiments, the concentration of the botulinum toxin in the liquid pharmaceutical composition preferably ranges from 50 to 5,000 units/mL depending on the general use thereof.

In certain embodiments, the liquid pharmaceutical composition using in the present invention has a pH of about 5.5 to 7.0. In certain embodiments, when the liquid pharmaceutical composition used in the present invention is adjusted to a pH of about 5.5 to about 7.0, botulinum toxin is stably maintained at room temperature (particularly 40° C.) for a long period of time.

The liquid pharmaceutical composition can be readily prepared because it employs a detergent and an amino acid(s) without a lyophilization process.

Lyophilized Animal-Protein-Free Botulinum Toxin Formulation

Compositions useful in the invention include an animal-protein-free botulinum toxin composition. In certain embodiments, the animal-protein-free botulinum toxin composition is a lyophilized preparation of botulinum toxin. For example, the lyophilized preparation of botulinum toxin composition useful in the invention does not contain a protein stabilizer derived from an animal.

In certain embodiments, the present invention provides a lyophilized preparation of a botulinum toxin composition comprising: 1) botulinum toxin; 2) polysorbate; 3) methionine; and 4) one or more components selected from a group consisting of sugar, sugar alcohol, an ionic compound, and a combination thereof.

In certain embodiments, when the botulinum toxin composition is formed as a lyophilized preparation, the component(s) play(s) a role in maintaining the activity of the botulinum toxin composition while facilitating stabilization at temperatures greater than room temperature. At the time of lyophilization, preparations containing 1) botulinum toxin; 2) polysorbate; and 3) methionine exhibit reduced stability, and when they are formulated as a liquid preparation they experience reduced stability at temperatures greater than room temperature; however, the lyophilized preparation of botulinum toxin composition used in certain embodiments of the present invention not only maintains the activity of the botulinum toxin composition at temperatures greater than room temperature, but also is excellent relative to storage stability over long periods.

The botulinum toxin may be derived from *Clostridium botulinum*. The botulinum toxin may be separated and refined from these strains by known methods, or else a commercially available product may be used.

The botulinum toxin may be randomly selected from a group consisting of botulinum Serotypes A, B, C, D, E F and G.

The botulinum toxin present in the lyophilized preparation may be in forms containing and not containing proteins in complexes. The activity of the botulinum toxin is unaffected whether or not the protein is in a complex. In the lyophilized preparation of botulinum toxin composition used in certain embodiments of the present invention, polysorbate, which is one of the stabilizers of the botulinum toxin, is a non-ionic surfactant, and is primarily used as an emulsifier in the pharmaceutical or food industries. As polysorbate types, there are polysorbate 20, 40, 60, 80 or 100, based on the total number of oxyethylene groups. For the lyophilized preparation of botulinum toxin composition used in certain embodiments of the present invention, it is acceptable to use any from among these. The polysorbate may be present at an amount of about 0.01 to about 2 mg per 100 units of the botulinum toxin. If polysorbate is present within this range, then the activity of the botulinum toxin can be maintained even at temperatures greater than room temperature, and long-term storage stability can be maintained.

In certain embodiments, methionine, which is one of the stabilizers, may also be used as a substitute for animal proteins such as albumin or gelatin, as the stabilizer for the botulinum toxin. The methionine may be present at an amount of about 0.01 to 10 mg per 100 units of the botulinum toxin. If methionine is comprised within this range, then the activity of the botulinum toxin composition can be maintained even at temperatures greater than room temperature, and long-term storage stability can be maintained.

Different from existing liquid preparations, the lyophilized preparation of botulinum toxin composition used in certain embodiments of the present invention further comprises at least one from among sugar, sugar alcohol or an ionic compound, as an additional component aside from methionine and polysorbate. Sugar is known to protect the denaturation of the macromolecule. As a sugar that may be used in the lyophilized preparation used in certain embodiments of the present invention, trehalose, sucrose, maltose, fructose, lapinose, lactose or glucose may be used; however, the use thereof is not limited to these types. The sugar may be at an amount of about 0.1 to 50 mg per 100 units of the botulinum toxin. If sugar is present within this range, then the activity of the botulinum toxin composition can be maintained even at temperatures greater than room temperature, and long-term storage stability can be maintained.

Sugar alcohol is known to stabilize the macromolecule under lyophilization conditions, and to usefully prevent denaturation. As a sugar alcohol that may be used in the lyophilized preparation used in certain embodiments of the present invention, cyclodextrin, mannitol, sorbitol, glycerol, xylitol or inositol, etc. may be used. The sugar alcohol may be at an amount of about 0.1 to 50 mg per 100 units of the botulinum toxin. If sugar alcohol is present within this range, then the activity of the botulinum toxin composition can be maintained even at temperatures greater than room temperature, and long-term storage stability can be maintained.

In certain embodiments, "ionic compound" refers to a salt, buffer, etc. The ionic compound works with the macromolecule through specific or non-specific binding. Salt can increase thermal stability, increase solubility and decrease the degree of aggregation. However, caution is required with high concentrations of salt due to the observed tendency for protein denaturation. As the ionic compound, sodium chloride, sodium phosphate, ammonium phosphate, magnesium sulfate, sodium acetate, sodium lactate, sodium succinate, sodium propionate or potassium phosphate may be used; however, the use thereof is not limited to these types. The ionic compound may be present at an amount of about 0.1 to 10 mg per 100 units of the botulinum toxin. If the ionic compound is present within this range, then the activity of the botulinum toxin composition can be maintained even at temperatures greater than room temperature, and long-term storage stability can be maintained.

In certain embodiments, the lyophilized preparation of botulinum toxin composition used in the present invention is manufactured from the culture of *Clostridium botulinum* that has been cultured in a specific medium, although this is not limited. The botulinum toxin complex is purified through a series of acid precipitations as a crystalline complex composed of active high molecular weight toxin protein and related Hemagglutinin protein. The crystalline complex is dissolved in a solution containing salt and stabilizer, and the lyophilized preparation of botulinum toxin composition is produced by undergoing a freeze drying process.

Method

The invention relates to the use of an animal-protein-free botulinum toxin composition to treat a disease, disorder or condition in a patient in need thereof whereby the animal-protein-free botulinum toxin composition exhibits a longer lasting effect in the patient compared to an animal-protein-containing botulinum toxin composition. For example, it was observed that an animal-protein-free botulinum toxin composition exhibited a greater improvement on the therapeutic outcome in a patient compared to the outcome of the patient receiving an animal-protein-containing botulinum toxin composition.

In certain embodiments, the efficacy of the animal-protein-free botulinum toxin composition (e.g., a liquid formulation or a lyophilized form) persists longer in the patient compared to an animal-protein-containing botulinum toxin composition. In certain embodiments, the administration of the animal-protein-free botulinum toxin composition (e.g., a liquid formulation or a lyophilized form) allows for larger interval time between administrations of the botulinum toxin composition compared to the interval time when using an animal-protein-containing botulinum toxin administered at the same or comparable dose and at the same or comparable sites.

In certain embodiments, the invention provides a treatment regimen that includes using an animal-protein-free botulinum toxin composition wherein the botulinum toxin composition is administered to a patient in need thereof at a lower dose compared to the dose used with an animal-protein-containing botulinum toxin composition.

In certain embodiments, the invention provides a method for treating a condition in a patient in need thereof, the method comprising the step of locally administering a therapeutically effective amount of an animal-protein-free botulinum toxin composition, whereby at least one symptom of the condition is thereby effectively alleviated for a period of time longer than that of an animal-protein-containing botulinum toxin composition.

In certain embodiments, the invention provides a treatment regimen that includes using an animal-protein-free botulinum toxin composition wherein the botulinum toxin composition is administered to a patient in need thereof at a greater time interval between administrations compared to the time interval used with an animal-protein-containing botulinum toxin composition.

In certain embodiments, the invention provides a method for treating a condition in a patient in need thereof, the method comprising the step of locally administering a therapeutically effective amount of an animal-protein-free botulinum toxin composition, wherein the composition is administered at an interval of time between a first treatment and a second treatment effective to maintain alleviation of at least one symptom of the condition, that is greater than the interval of time for an animal-protein-containing botulinum toxin composition dosed at the same or comparable amount and administered in the same manner (e.g. by injection) to the same locations as that of the animal-protein-free composition.

In certain embodiments, the time between the first treatment and second treatment of a condition in a human patient using an animal-protein-free botulinum toxin composition is at least one month, at least 2 months, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, at least 52 weeks or more. In certain embodiments, the time between the first treatment and second treatment using an animal-protein-free botulinum toxin composition is greater than 3 months for the effective alleviation of at least one symptom of a condition in a patient. In certain embodiments, the time between the first treatment and second treatment using an animal-protein-free botulinum toxin composition of the present invention is greater than 16 weeks for the effective alleviation of at least one symptom of a condition in a patient.

In certain embodiments, the animal-protein-free botulinum toxin composition of the present invention can be used for cosmetic purposes such as to treat skin contour deficiencies, including wrinkles, of an individual.

In certain embodiments, the animal-protein-free botulinum toxin composition of the present invention can be used to treat glabellar lines.

In certain embodiments, the animal-protein-free botulinum toxin composition of the present invention can be used to treat lateral canthal lines.

In certain embodiments, the animal-protein-free botulinum toxin composition of the present invention can be used for non-cosmetic purposes. In certain embodiments, the animal-protein-free botulinum toxin composition of the present invention can be used to treat various diseases and disorders including but not limited to detrusor overactivity associated with a neurologic condition, chronic migraine, upper limb spasticity, cervical dystonia, primary axillary hyperhidrosis, blepharospasm and strabismus, idiopathic overactive bladder, and the like.

In certain embodiments, the animal-protein-free botulinum toxin composition of the present invention can be used for non-cosmetic purposes. Non-limiting examples of a non-cosmetic purpose includes but is not limited to the treatment of urinary incontinence due to detrusor overactivity associated with a neurologic condition [e.g., spinal cord injury (SCI), multiple sclerosis (MS)] in adults who have an inadequate response to or are intolerant of an anticholinergic medication, prophylaxis of headaches in patients with chronic migraine (e.g., ≥15 days per month with headache lasting 4 hours a day or longer), treatment of upper limb spasticity in adult patients, treatment of cervical dystonia in adult patients, to reduce the severity of abnormal head position and neck pain, treatment of severe axillary hyperhidrosis that is inadequately managed by topical agents in adult patients, treatment of blepharospasm associated with dystonia, treatment of strabismus in patients ≥12 years of age.

However, the invention should not be limited to only the diseases, disorder, or conditions disclosed herein. Rather, the invention encompasses the use of the animal-protein-free botulinum toxin composition of the present invention to treat any disease for where botulinum toxin has been used. For example, botulinum toxin has been proposed for or has been used to treat otitis media of the ear (U.S. Pat. No. 5,766,605), inner ear disorders (U.S. Pat. Nos. 6,265,379; 6,358,926), tension headache, (U.S. Pat. No. 6,458,365), migraine headache pain (U.S. Pat. No. 5,714,468), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), and neurogenic inflammation (U.S. Pat. No. 6,063,768). In addition, botulinum toxins have been used in clinical settings for cosmetic applications as well as the treatment of neuromuscular disorders characterized by hyperactive skeletal muscles. Botulinum toxin is currently used in the treatment of hyperhidrosis, and can also be used in the treatment of achalasia, chronic focal neuropathies, anal fissure, vaginismus, spastic disorders associated with injury or disease of the central nervous system (including, for example, trauma, stroke, multiple sclerosis, Parkinson's disease, cerebral palsy, and the like), focal dystonias affecting the limbs, face, jaw, or vocal cords, temporomandibular joint disorder (TMJ), diabetic neuropathy, wound healing disorders, excessive salivation, vocal cord dysfunction (VCD) including spasmodic dysphonia, and tremor. Botulinum toxin type A has been approved by the U.S. Food and Drug Administration for the treatment of blepharospasm, strabismus, hemifacial spasm, cervical dystonia, migraine headaches, overactive bladder and detrusor overactivity associated with a neurological condition.

In certain embodiments, methods of the invention can be useful for the treatment, reduction of symptoms, and/or prevention of achalasia, anal fissure, anismus, blepharospasm, cerebral palsy, cervical dystonia, cervicogenic headache, hemifacial spasm, dyshidrotic eczema, dysphagia, dysphonia, esophageal dysmotility, esophageal muscular ring, esotropia (infantile), eyelift, facial myokymia, gait disturbances (idiopathic toe-walking), generalized dystonia, hemifacial spasm, hyperfunctional facial lines (glabellar, forehead, crows' feet, down-turned angles of the mouth), hyperhidrosis, incontinence (spinal cord injury), migraine headache, myoclonus, myofascial pain syndrome, obstructive urinary symptoms, pancreas divisum pancreatitis, Parkinson's disease, puborectalis syndrome, reduction of surgical scar tension, salivary hypersecretion, sialocele, sixth nerve palsy, spasticity, speech/voice disorders, strabismus, surgery adjunct (ophthalmic), tardive dyskinesia, temporomandibular joint disorders, tension headache, thoracic outlet syndrome, torsion dystonia, torticollis, Tourette's syndrome, tremor, whiplash-associated neck pain, pain, itching, inflammation, allergy, cancer and benign tumors, fever, obesity, infectious diseases, viral and bacterial, hypertension, cardiac arrhythmias, vasospasm, atherosclerosis, endothelial hyperplasia, venous thrombosis, varicose veins, aphthous stomatitis, hypersalivation, temporomandibular joint syndrome, sweating, body odor, acne, rosacea, hyperpigmentation, hypertrophic scars, keloid, calluses and corns, skin wrinkling, excessive sebum production, psoriasis, dermatitis, allergic rhinitis, nasal congestion, post nasal drip, sneezing, ear wax, serous and suppurative otitis media, tonsil and adenoid hypertrophy, tinnitus, dizziness, vertigo, hoarseness, cough, sleep apnea, snoring, glaucoma, conjunctivitis, uveitis, strabismus, Grave's disease, asthma, bronchitis, emphysema, mucus production, pleuritis, coagulation disorders, myeloproliferative disorders, disorders involving eosinophils, neutrophils, macrophages and lymphocytes, immune tolerance and transplantation, autoimmune disorders, dysphagia, acid reflux, hiatal hernia, gastritis and hyperacidity, diarrhea and constipation, hemorrhoids, urinary incontinence, prostatic hypertrophy, erectile dysfunction, priapism and Peyronie's disease, epididymitis, contraception, menstrual cramps, preventing premature delivery, endometriosis and fibroids, arthritis, osteoarthritis, rheumatoid, bursitis, tendonitis, tenosynovitis, fibromyalgia, seizure disorders, cerebral palsy, spasticity, headache, depression and neuralgias.

In certain embodiments, the treatment regimen of the invention comprises local administration of the animal-protein-free botulinum toxin composition. In certain embodiments, the treatment regimen comprises parenteral administration of the animal-protein-free botulinum toxin composition. In certain embodiments the animal-protein-free composition is administered by injection, topically or by implantation of a controlled release implant. Examples of administration by injection include intramuscular injection, non-intramuscular injection, intra-articular injection, extra-articular injection, peri-articular injection, or subcutaneous injection.

In certain embodiments, the treatment regimen of the invention is beneficial due to the longer lasting effect and improved outcomes associated with using animal-protein-free botulinum toxin compositions when compared to using animal-protein-containing botulinum toxin compositions. Without wishing to be bound by any particular theory, it is believed that in certain embodiments the long lasting effect of the animal-protein-free botulinum toxin composition allows for a longer interval time between treatments with the animal-protein-free botulinum toxin composition compared to the interval time when using an animal-protein-containing botulinum toxin composition.

Furthermore, without wishing to be bound by any particular theory, it is believed that in certain embodiments the unique formulation of the compositions using in the invention allows for the longer lasting effect of the composition in the patient.

In certain embodiments, by increasing the interval time between treatments, the treatment regimen allows for a reduction in the frequency of treatment. Therefore, the invention provides the potential for enhanced patient convenience. The increased interval time between treatment and lower frequency of treatment also has the potential to provide reduced side effects.

In certain embodiments, the treatment regimen of the invention is beneficial due to the long lasting effect and improved outcomes associated with using the liquid animal-protein-free botulinum toxin composition or the lyophilized animal-protein-free botulinum composition as described herein.

In certain embodiments, in a treatment method of the invention, a therapeutically effective level botulinum toxin is present in the recipient patient for an extended period of time of at least 16 weeks, at least 18 weeks, at least 20 weeks, at least 22 weeks, at least 24 weeks, at least 26 weeks, at least 28 weeks, at least 30 weeks, at least 32 weeks, at least 34 weeks, at least 36 weeks, at least 38 weeks, at least 40 weeks, at least 42 weeks, at least 44 weeks, at least 46 weeks, at least 48 weeks, at least 50 weeks, or more.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: The Efficacy and Safety of Liquid Type Botulinum Toxin Type A for the Management of Moderate to Severe Glabellar Frown Lines: A Parallel, Randomized, Double-Blind, Multi-Center, Active Drug Controlled, Phase III Clinical Trial Botulinum toxin A (BoNT/A) has been used widely in a variety of manners to correct unwanted glabellar lines and other hyperfunctional facial lines. However, most of currently using BoNT/A requires dilution with saline solution, which is very inconvenient for the user, and usually is hard to make the exact concentration every time. The results presented herein is based on experiments conducted that compared the efficacy and safety of newly developed liquid type BoNT/A (MT10109L) and onabotulinumtoxinA (BOTOX®; ona-BoNT/A) for moderate to severe glabellar lines.

The materials and methods employed in these experiments are now described.

Materials and Methods

This study was a prospective, randomized, double-blind, parallel, active drug controlled, Phase III clinical trial for the evaluation of the efficacy and safety of MT10109L on the glabellar frown line correction which was performed in three centers (St. Paul's hospital, Catholic university of Korea; Inha university hospital; Kyunghee university hospital at Gangdong) in South Korea. The study and all appropriate amendments were reviewed and approved by the institutional review board at each participating center in accordance with the guidelines published in the Declaration of Helsinki (South Africa, 1996 amendment) and Good Clinical Practice guideline. All participants gave written informed consent to take part in the study.

Participants

Male and female volunteers aged 20-65 years with glabellar lines were screened by investigators. According to Facial Wrinkle Scale (FWS), subjects with moderate to severe (severity score 2 to 3) glabellar frown lines were enrolled in this study (Table 1). Exclusion criteria included any medical condition (e.g. myasthenia gravis, Lambert-Eaton syndrome, amyotrophic lateral sclerosis) that may place the patient at risk with botulinum toxin, prior use of medications that may affect the neuromuscular junction (e.g., muscle relaxants, spectinomycin HCl, aminoglycosides, polypeptide antibiotics, anticholinergics, benzodiazepines) or any allergies or hypersensitivity to the investigational drugs or their components. Other exclusion criteria included previous treatment with botulinum toxin within 3 months, other procedures that may have affected glabellar and forehead lines within 6 months, any history of glabellar treatment (including forehead) such as face lifting and/or permanent implants, or scars that may affect the treatment results. Patients whose glabellar lines that could not be satisfactorily improved even with manual stretching were also excluded. Patients were not eligible if they had dermatological disorders or infection at potential injection sites, or a history of facial nerve paralysis or ptosis. Pregnant or lactating women were excluded.

TABLE 1

Scales used to assess the effectiveness of MT10109L and Ona-BoNT/A

| Measure | scale | Description |
|---|---|---|
| Facial Wrinkle Scale, maximal frown | 3 | Severe; lines appear clearly formed. The bottoms of the deepest lines are |
|  | 2 | Moderate; lines appear clearly formed. The bottoms of the deepest lines |
|  | 1 | Mild; lines noted |
|  | 0 | None; lines not noted |
| Facial Wrinkle Scale, rest | 3 | Severe; lines readily apparent |
|  | 2 | Moderate; lines noticeable |
|  | 1 | Mild; lines somewhat noticeable |
|  | 0 | None; lines not noticeable |

Study Design

Figure 2:
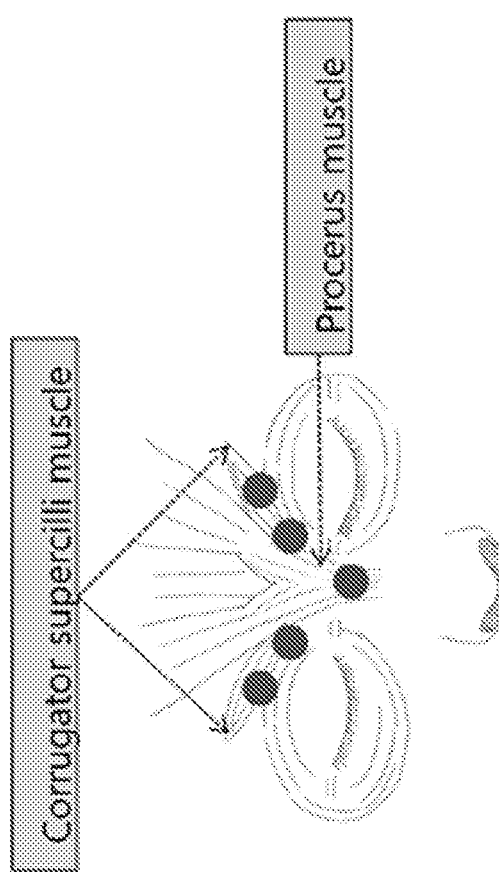
FIG. 2 is an image showing the injection sites. The glabellar lines received a single session of either MT10109L or ona-BoN/T. The 0.5 mL (20 U) total injection volume was divided into five symmetrical intramuscular injections: 0.1 mL (4 U) in the procerus muscle, 0.1 mL (4 U) in each medial corrugator supercilii muscles, and 0.1 mL (4 U) in the middle of each corrugator supercilii muscles.

All eligible subjects were randomized into two groups at a 1:1 ratio and followed a 16 weeks duration study design (FIG. 1.). At Visit 2 (0 week, baseline), each subject received a 5 point intramuscular injection with a total dose of 20 U (4 U/0.1 ml) of liquid BoNT/A (MT10109L; Medytox Inc., Cheongwon-gun, Korea) or onabotulinumtoxinA (BO-TOX®; ona-BoNT/A) in a double blind manner. The 0.5 mL total injection volume was divided into five injections: 0.1 mL (4 U) in the procerus muscle, 0.1 mL (4 U) in each medial corrugator supercilii muscles, and 0.1 mL (4 U) in the middle of each corrugator supercilii muscles (FIG. 2). For this clinical study, MT10109L (0.625 ml/vial (4 U/0.1 ml)) and 50 U ona-BoNT/A was used. MT10109L did not require additional dilution for its liquid nature, but ona-BoNT/A was dissolved in 1.25 ml of 0.9% NaCl 1.25 ml to make it 4 U per 0.1 ml.

Efficacy Measures

During the observation period of 16 weeks, the subjects were assessed at 4, 10, 16 weeks. At each visit, both the investigator and the patient assessed efficacy and safety. In addition, standardized digital photographs of the treated facial area were taken in the same setting using the same equipment (EOS 600d, Canon Inc., Tokyo, Japan) to ensure reproducibility (FIG. 1). Physicians assessed the glabellar line severity at maximum frown and at rest using FWS by live assessment. All investigators in each center were provided the standardized photograph grading system. Three blinded raters assessed the photographs at maximum frown and at rest according to the FWS (Table 1).

The primary efficacy end point was the percentage of responders at maximum frown at week 4 based on the investigator's live assessment (face-to-face observation). Secondary efficacy end point included: 1) percentage of responders at maximum frown at weeks 16; 2) percentage of responders of glabellar lines at rest based on investigator's live assessment at weeks 4 and 16; and 3) percentage of responders at maximum frown and at rest based on photographic assessment at weeks 4. In accordance with previous studies for ona-BoNT/A, responders were defined as those who have post-treatment FWS scores of 0 or 1 with pre-treatment FWS scores of 2 or 3. This means an improvement of at least 1 point for the subjects with moderate wrinkles and at least 2 points for the subjects with severe wrinkles. In addition, the glabellar line improvement rates determined by the subject's own assessment and satisfaction rates at weeks 4, 10 and 16 as secondary efficacy end point were also included. Subjects assessed the change of the line severity using 9 point scale from +4 (100% improvement) to 0 (no change) to −4 (100% worse), and rated their degree of satisfaction with the treatment in a 7 point scale from −3 (very unsatisfied) to +3 (very satisfied). Scores of more than +2 points (moderately improved) was considered as improvement. Moreover, scores of more than 6 points (satisfied) were considered as satisfaction.

Safety Measures

During the study, physical examination and vital sign were checked every visit. Investigator- and subject-reported signs and symptoms, and laboratory test (Complete Blood Count, and Blood Chemistry) were performed at screening day and weeks 16. Urine-hCG was checked at screening, treatment day, and week 16. Summary and analysis of adverse events was performed about all adverse events occurred after receipt of consent. Incidence of adverse events were documented by comparing incidence of all adverse events, incidence of adverse events related to study drug, and incidence of severe adverse events.

Statistical Methods

All subjects with data for primary end points were included in the full analysis set (FAS). The per protocol (PP) set was the subset of subjects of the FAS who did not commit any major protocol violation. For the primary efficacy end point parameter, the lower limit of 97.5% one-sided confidential interval (CI) for the difference in responder rates between two groups was calculated. The interpretation of the CI was based on the null hypothesis that the expected difference in responder rates between the treatment groups was lower than the non-inferiority margin of −15%. If the lower bound of the estimated CI exceeded the limit of −15%, one could conclude that the MT10109L was not inferior to ona-BoNT/A. This confirmatory analysis was based on the PP analysis. For secondary efficacy end point, paired t-test, Pearson's chi-square test, or Fisher's exact test were performed.

Fisher's exact test was performed to test for between-group differences in adverse events. For laboratory variables, blood pressure, and heart rate, the Wilcoxon signed-rank test was performed for within-group analyses, and the Wilcoxon rank-sum test was used for between group analyses of data at exit.

The results of the experiments are now described.

Baseline Demographic Characteristics

Of 168 subjects enrolled, 159 subjects completed the study and therefore constituted the PP set: 78 subjects in MT10109L group and 81 subjects in ona-BoNT/A group. The enrolled subject's age was from 20 to 65, and the mean age was 48.94 year old in MT10109L group and 49.86 year old in ona-BoNT/A group, respectively. All subjects were Koreans. Demographics of the two groups were comparable, and two groups did not differ in their pretreatment line severity either at rest or maximum frown before treatment. All of subjects had moderate to severe glabellar frown lines at rest and the majority of subjects had severe glabellar frown lines at maximum frown (56.41% for MT10109L group; 50.62% for ona-BoNT/A group) (Table 2).

TABLE 2

Subject Demographic Characteristics (N = 159, PP set)

| | | MT10109L<br>N = 78<br>n (%) | Ona-BoNT/A<br>N = 81<br>n (%) | p-value |
|---|---|---|---|---|
| Age | n | 78 | 81 | |
| | Mean ± SD | 48.94 ± 9.13 | 49.86 ± 9.13 | 0.5226* |
| | 20~29 | 3(3.85) | 3(3.70) | 0.8081† |
| | 30~30 | 7(8.97) | 9(11.11) | |
| | 40~49 | 25(35.90) | 22(27.16) | |
| | 50~59 | 32(41.03) | 39(48.15) | |
| | 60~65 | 8(10.26) | 8(9.88) | |
| Gender | n | 78 | 81 | |
| | male | 19(24.36) | 15(18.52) | 0.3692† |
| | female | 59(75.64) | 66(81.48) | |
| Botulinumtoxin injections history | n | 78 | 81 | |
| | yes | 15(19.23) | 12(14.81) | 0.4525† |
| | no | 63(80.77) | 69(85.19) | |
| No. of Botulinumtoxin injections | n | 15 | 12 | |
| | Mean ± SD | 1.93 ± 0.26 | 2.00 ± 0.43 | 0.6547† |
| Elapsed time after the administration of botulinumtoxin injections (month) | n | 15 | 12 | |
| | Mean ± SD | 22.18 ± 13.28 | 20.31 ± 16.44 | 0.6428+ |
| at screening, investigator's live assessment at maximum frown (point) | n | 78 | 81 | |
| | 3 (severe) | 44(56.41) | 41(50.62) | 0.4641† |
| | 2 (moderate) | 34(43.59) | 40(49.38) | |

*two sample t-test
+Wilcoxon rank sum test
†Pearson's chi-square test

Investigator's Assessment

Figure 3B:
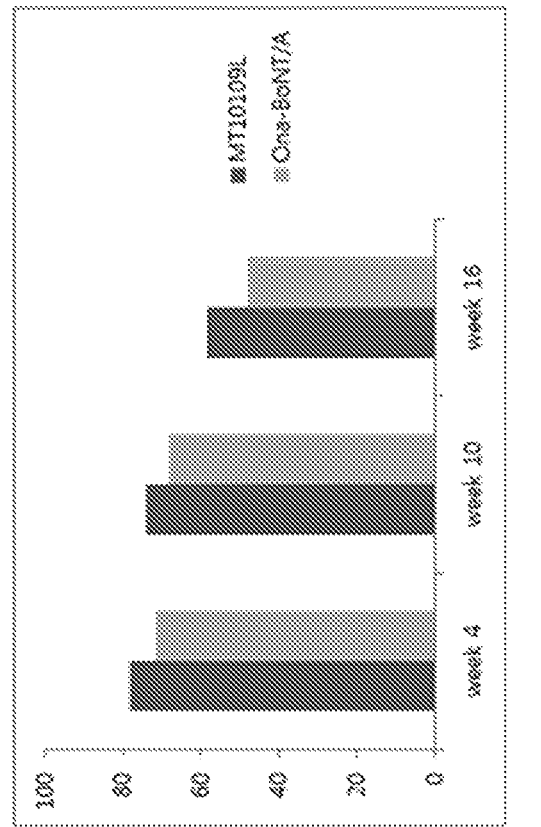
FIGS. 3A and 3B, is a series of images showing responder rate at maximum frown by live assessment (FIG. 3A) PP set and (FIG. 3B) FAS set.
Figure 3A:
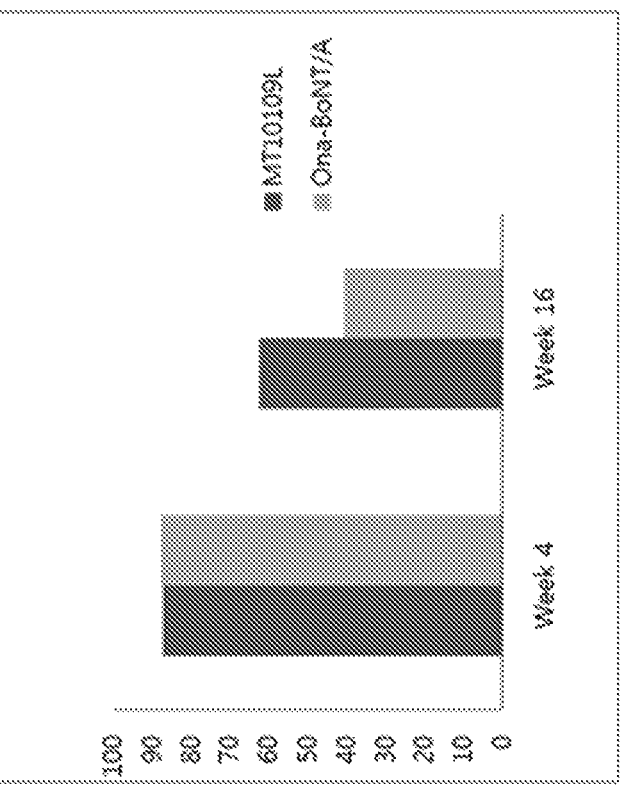

Both groups showed significant improvement of glabellar lines. Four weeks after injection, percentage of responders at maximum frown by live assessment for the PP set was 87.18% in MT10109L group and 87.65% in ona-BoNT/A group. In addition, percentage of responders of FAS in MT10109L group and ona-BoNT/A group was similar to that of PP set, being 85.54% and 85.71%, respectively (FIG. 3A). The 97.5% CIs for the difference in percentage of responders between the two treatment groups (−10.79% for PP>−15%; −10.47% for FAS>−15%) demonstrates that MT10109L was not inferior to ona-BoNT/A.

The percentage of responders at maximum frown by live assessment at weeks 16 was significantly lower in ona-BoNT/A group than MT10109L group. The percentage of responders in PP set was 62.34% in MT10109L group and 40.51% in ona-BoNT/A group (p value=0.0064) (Table 3). And the percentage of responders in FAS set was 60.71% in MT10109L group and 41.67% in ona-BoNT/A group (Table 3, FIG. 3B). Both PP set and FAS set showed significant difference in two groups and superiority of MT10109L.

The percentage of responders at rest was assessed at week 4 and 16, and no significant difference was noted between the MT10109L group and ona-BoNT/A group at week 4 in both PP set and FAS set. At week 16, percentage of responders at rest in PP set was 50.00% in MT10109L group and 31.58% in ona-BoNT/A group, showing significant improvement in MT10109L group (p value=0.0482). However, in the FAS set, the percentage of responders did not show significant difference between the MT10109L group (50.00%) and the ona-BoNT/A group (33.33%). (p value: 0.0641) (Table 3).

TABLE 3

Responder rate by live assessment at maximum frown

| | | | MT10109L<br>n (%) | Ona-BoNT/A<br>n (%) | p-value |
|---|---|---|---|---|---|
| PP set | | | N = 78 | N = 81 | |
| Week 4 | Improvement | n | 78 | 81 | |
| | | Responder | 68 (87.18) | 71 (87.65) | 0.9281† |
| | | non-responder | 10 (12.82) | 10 (12.35) | |
| | Facial Wrinkle Scale | 3 | 1 (1.28) | 0 (0) | |
| | | 2 | 9 (11.54) | 10 (12.35) | |
| | | 1 | 39 (50) | 44 (54.32) | |
| | | 0 | 29 (37.18) | 27 (33.33) | |
| Week 16 | Improvement | n | 77 | 79 | |
| | | Responder | 48 (62.34) | 32 (40.51) | 0.0064† |
| | | non-responder | 29 (37.66) | 47 (59.49) | |
| | Facial Wrinkle Scale | 3 | 8 (10.39) | 8 (10.13) | |
| | | 2 | 21 (27.27) | 39 (49.37) | |
| | | 1 | 36 (46.75) | 25 (31.65) | |
| | | 0 | 12 (15.58) | 7 (8.86) | |
| FAS set | | | N = 84 | N = 84 | |
| Week 4 | Improvement | n | 83 | 84 | |
| | | Responder | 71 (85.54) | 72 (85.71) | 0.9747† |
| | | non-responder | 12 (14.46) | 12 (14.29) | |
| | Facial Wrinkle Scale | 3 | 1 (1.2) | 1 (1.19) | |
| | | 2 | 11 (13.25) | 11 (13.1) | |
| | | 1 | 41 (49.4) | 45 (53.57) | |
| | | 0 | 30 (36.14) | 27 (32.14) | |
| Week 16 | Improvement | n | 84 | 84 | |
| | | Responder | 51 (60.71) | 35 (41.67) | 0.0135† |
| | | non-responder | 33 (39.29) | 49 (58.33) | |
| | Facial Wrinkle Scale | 3 | 8 (9.52) | 9 (10.71) | |
| | | 2 | 25 (29.76) | 40 (47.62) | |
| | | 1 | 39 (46.43) | 26 (30.95) | |
| | | 0 | 12 (14.29) | 9 (10.71) | |

†Pearson's chi-square test

In photographic assessment, the responder rate at maximum frown at weeks 4 by three independent, blinded raters also did not show significant difference between the MT10109L group and the ona-BoNT/A group in PP set and FAS set. The results are shown in Table 4.

TABLE 4

Responder rate by photo assessment (Weeks 4)

| | | | MT10109L n (%) | Ona-BoNT/A n (%) | p-value |
|---|---|---|---|---|---|
| Maximum frown | PP set | n | 78 | 81 | |
| | | Responder | 74 (94.87) | 79 (97.53) | 0.4369‡ |
| | | non-responder | 4 (5.13) | 2 (2.47) | |
| | FAS set | n | 83 | 84 | |
| | | Responder | 79 (95.18) | 82 −97.62 | 0.4431‡ |
| | | non-responder | 4 (4.82) | 2 −2.38 | |
| Resting | PP set | n | 44 | 47 | |
| | | Responder | 25 (56.82) | 25 (53.19) | 0.7282† |
| | | non-responder | 19 (43.18) | 22 (46.81) | |
| | FAS set | n | 48 | 49 | |
| | | Responder | 26 (54.17) | 25 (51.02) | 0.7564† |
| | | non-responder | 22 (45.83) | 24 (48.98) | |

Subject's Assessment

Figure 4A:
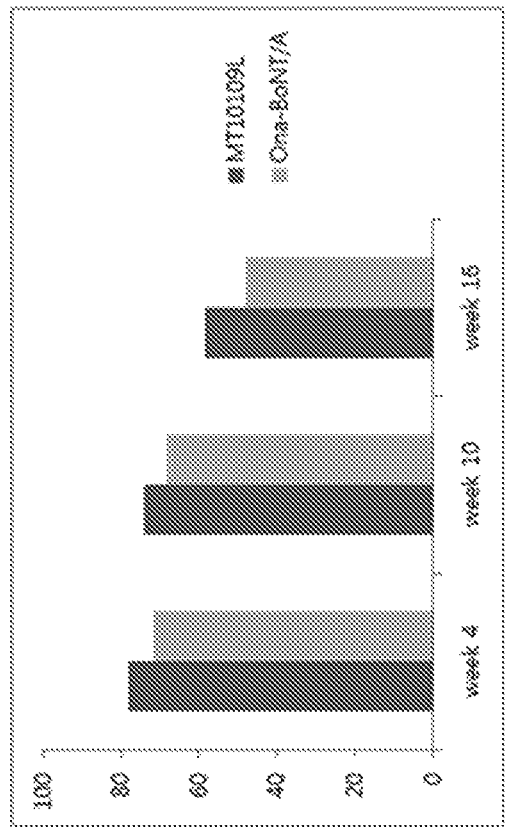
FIGS. 4A and 4B, is a series of images showing (FIG. 4A) responder rate by subject's assessment (PP set) and (FIG. 4B) subject's satisfaction rate (PP set).
Figure 4B:
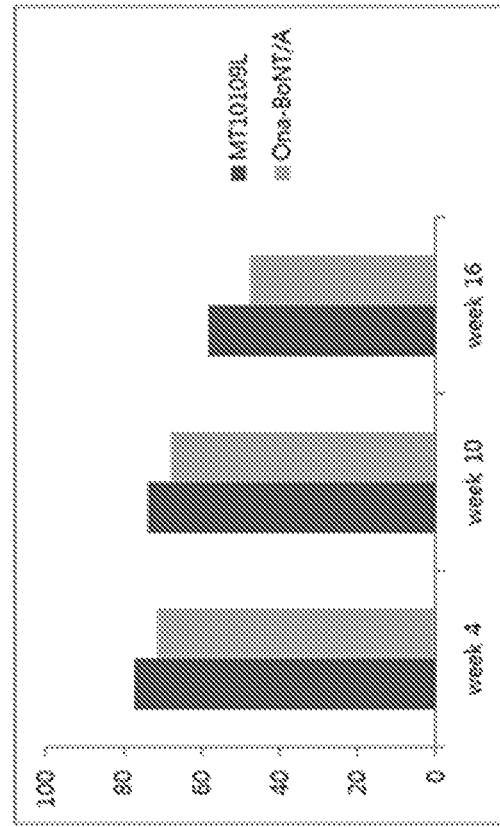

Subject's assessment on improvement of glabellar line and satisfaction yielded comparable results for both groups. Peak improvement rate defined as the proportion of subjects who scored more than +2 points (moderately improved) were assessed at week 4, 10, and 16. In both PP and FAS set, the peak improvement rate at week 4, 10, and 16 did not show significant difference between MT10119L and ona-BoNT/A groups. Subjective-assessment improvement rate was shown 89.74% and 92.59% at week 4, 81.82% and 91.14% at week 10, 70.13% and 68.35% at week 16, respectively in MT10109L and ona-BoNT/A group of PP set. Satisfaction rate defined as patient showing "very satisfied" or "satisfied" was assessed at week 4, 10, 16, and this also did not show significant difference in PP set and FAS set between MT10109L and ona-BoNT/A groups. Satisfaction rate was 78.21% and 71.60% at week 4, 74.03% and 68.35% at week 10, 58.44% and 48.10% at week 16, respectively in MT10109L and ona-BoNT/A group of PP set. The results of PP set are shown in FIG. 4.

Safety

Comparable numbers of treatment-emergent adverse events were reported in the MT10109L group (21.43%) and the control group (16.67%) (Table 5). There was no adverse drug reaction in MT10109L group. The only adverse drug reaction related to injection was one incident of face edema reported in the control group. No severe adverse drug reaction was observed in both groups. No subjects were withdrawn because of adverse events.

TABLE 5

Adverse events (safety set)

| adverse events (n, %) | MT10109L group (N = 84) | Ona-BoNT/A (N = 84) | p-value |
|---|---|---|---|
| adverse events | 19 (22.62) | 15 (17.86) | 0.4424 |
| treatment-emergent adverse events | 18 (21.43) | 14 (16.67) | 0.4319 |
| adverse drug reaction | | | |
| facial edema | 0 (0.00) | 1 (1.19) | 1 |
| severe adverse events | | | |
| acute myocardial infarction | 0 (0.00) | 1 (1.19) | 1 |
| peritonitis | 0 (0.00) | 1 (1.19) | 1 |
| rotator cuff syndrome | 1 (1.19) | 0 (0.00) | 1 |

Serious adverse events happening after the patient receiving the test medication were reported in 1.19% (1/84 subjects, 1 incidents) of the MT10109L group and 2.38% (2/84 subjects, 2 incidents) of the control group. For serious adverse events, acute myocardial infarction and peritonitis was reported in each patient of ona-BoNT/A group. The patient who developed acute myocardial infarction have been treated for his cardiac problem in the cardiology department, thus, this event does not seem to be related to test drug injection. And Rotator cuff syndrome was reported in one patient of MT10109L group after the patient received the test medication.

In terms of the laboratory tests and vital signs, no significant abnormal changes were detected after the test drug administration in MT10109L group and ona-BoNT/A group.

The Efficacy and Safety of Liquid Type Botulinum Toxin Type A

The results presented herein demonstrate that MT10109L is safe and effective for the treatment of glabellar lines. MT10109L treatment resulted in significant improvement of glabella frown line severity at both maximal contraction and rest by live assessment at week 4 and week 16. The results of photographic assessment by blinded raters and subject's assessment in this study indicate that ona-BoNT/A and MT10109L did not differ significantly in any variable at any point. The result also showed that MT10109L may provide greater improvement than ona-BoNT/A at week 16. The results presented here also suggest that efficacy of MT10109L persisted longer than ona-BoNT/A.

Commercially available BoNT/A preparations were very diverse and had different efficacies and safety because of their unique biologic nature (Klein A W, et al., Plast Reconstr Surg., 2008; 121(6):413e-422e). Of these, ona-BoNT/A is the best known type which dominates the botulinum toxin market since it was first approved and marketed in the United States in 1989 (Yang G H, et al., Dermatologic Surgery, 2013; 39(1pt2):165-170). As a consequence, the majority of the information about handling botulinum toxin type A is found with ona-BoNT/A (Trindade De Almeida A R, et al., Dermatologic Surgery, 2011; 37(11):1553-1565), Thus, this study was designed to compare the efficacy and safety of MT10109L and ona-BoNT/A.

All of the currently used BoNT/A products recommend that reconstitution be performed using variable substances before injection since the products are provided as freeze dried powder formulation. These products also have discommodity on supply, dilution and storage. For example, Ona-BoNT/A should be stored between 2° C. and 8° C. after reconstitution, and is to be used within 24 hours of reconstitution (Huang W, et al., J Am Acad Dermatol 2000; 43:249-59).

Although rimabotulinumtoxin b (Myobloc®, Solstice Neurosciences, Louisville, KY) has been used as liquid injection form of botulinum toxin B, it is not widely used as much as BoNT/A and the equivalent dosage of rimabotulinumtoxin b with BoNT/A has not been fully studied (Trindade De Almeida A R, et al., Dermatologic Surgery, 2011; 37(11):1553-1565).

MT10109L is the first liquid injection form of BoNT/A. MT10109L contains BoNT/A type macromolecular protein complexes with molecular weights of 900 kD, which is similar to ona-BoNT/A (Table 6). MT10109L exhibits a similar diffusion capacity to that of ona-BoNT/A.

MT10109L is provided as a ready-to-use sterile liquid; no reconstitution is required and is more convenient to store and reuse compared to most of BoNT/A. The shelf life of MT10109L is currently estimated at around 22 months from the date of manufacture, however, without wishing to be bound by any particular theory, it is expected to be prolonged through extended stability test. During the period, MT10109L can be reused at anytime without time limit, whereas ona-BoNT/A is recommended to be used within 4 hours to 6 weeks after reconstitution (Carruthers J, et al., Plast Reconstr Surg., 2004; (Suppl); 11(6)4:2S and Hexsel D M, et al., Dermatol Surg., 2003; 29:523-9). Because longer stability of MT10109L is validated as mentioned elsewhere herein, MT10109L has an advantage over reconstituted ona-BoNT/A in reusing. Moreover, MT10109L is currently available as small package unit (25 U/vial), which is suitable for treatment of glabellar lines (Table 6).

| Characteristics of botulinum Toxin Preparations | | |
|---|---|---|
| | MT10109L | Ona-BoNT/A |
| Manufaturer | Medytox Inc. | Allergan, Inc. |
| Commercial names | Neuranox Aqua ® | Botox ®, Botox cosmetic ®, Vistabel ®, Vistabex ® |
| Toxin serotype | A | A |
| Indications | glabellar lines | Blepharospasm, cervical dystonia, glabellar lines, hyperhidrosis, chronic migraine |
| Active substance | Botulinum Toxin Type A | Botulinum Toxin Type A |
| Complex molecular weight | 900 kDa | 900 kDa |
| U/vial | 25 | 50 |
| Stabilizer/vial | methionine (0.125 mg) polysorbate 20 (0.094 mg) | Human serum albumin (0.5 mg) |
| Excipients/vial | sodium chloride (5.625 mg) | sodium chloride (0.45 mg) |
| Formulation | liquid | vacuum-dried powder |
| Dilution, mL | No reconstitution required | 1.0-2.5 |
| Storage | 2-8° C. | 2-8° C. or <−5° C. |
| Storage after dilution/temperature | without limitation/2-8° C. | 24 hours/2-8° C. |

The results presented herein demonstrate that the efficacy of MT10109L persisted longer than ona-BoNT/A. The therapeutic effect of BoNT/A for the glabellar line improvement could be detected within 4 weeks after injection and gradually decrease between 3-6 months. The fact that a longer maintaining period of the glabellar line improvement associated with the use of MT10109L provides a great advantage over other types of BoNT/A. Results from a meta-analysis by Glogau R, et al. showed treatment of glabellar line with 20 unit of ona-BoNT/A sustained clinical effect at week 16 in more than 50% of responders (Glogau R, et al., Dermatol Surg., 2012; 38(11):1794-803). However, in this study, responder rate of ona-BoNT/A was lower than that of previous reports. Thus, large studies, with enrollment of patients from several medical centers and with longer follow-up periods, are needed to confirm this result.

Whereas currently used BoNT/A contain albumin or gelatin for stabilization, MT10109L eliminated albumin but also animal derived materials in component of the entire manufacturing process. Therefore, MT10109L minimized risk of infectious diseases which included transmissible spongiform encephalopathy. No severe adverse drug reactions with either toxin were observed in the present study. Therefore, MT10109L is as safe as ona-BoNT/A.

The results presented herein demonstrate that MT10109L is not inferior to ona-BoNT/A in the improvement of glabellar lines and is relatively similar in safety, which therefore can be judged to be used in the treatment of the relevant symptom. With its longer maintaining period of the glabellar line improvement, convenience without the additional dilution step, easy storage and re-usage, and animal derived protein-free constituents, MT10109L is a desirable substitute for the conventional powder formulation of BoNT/A.

Example 2: Randomized, Double-Blind, Multi-Center, Phase II, Optimal Dose-Finding Study to Determine Safety and Efficacy of MT10109 v. BOTOX in Subjects with Moderate to Severe Glabellar Lines The results presented herein compare the safety and efficacy of lyophilized formulation of MT10109 and BOTOX® in subjects with moderate to severe glabellar lines. It is demonstrated that the response at maximum frown was sustained in the MT10109 20 U group for up to 120 days.

The experiments described herein compared dosing of MT10109 at 10 U, 20 U and 30 U to BOTOX® dosed at 20 U. The efficacy of MT10109 was primarily assessed at Day 30 (Visit 4; ±7 days) and the comparison of interest was the comparison between the responder rates for MT10109 20 U and BOTOX® 20 U. A responder was defined as a glabellar line severity rating of none (0) or mild (1) at maximum frown or at rest at Day 30, depending on the analysis.

The time points of Day 14 (Visit 3), Day 30 (Visit 4), Day 60 (Visit 5), Day 90 (Visit 6) and Day 120 (Visit 7) were allowed 7 days either side of the visit day and so Day 30, for example, may not be exactly 30 days after study treatment administration. As presented herein, time points have been labelled by day rather than visit. All analyses of efficacy were performed using the Full Analysis Set (FAS) and were repeated using the Per-protocol (PP) Set as a supportive analysis.

Primary Efficacy Parameter: Investigator's Rating of Glabellar Line Severity at Maximum Frown at Day 30 by Live Assessment The investigator's live assessment of glabellar line severity at maximum frown at Day 30 is summarized for the FAS in Table 7. A Mantel-Haenszel chi-square test was used to compare treatment groups and is in diagram form in FIG. 5. Results for the PP Set are summarized in Table 8.

TABLE 7

Investigator's Live Assessment of Glabellar Line Severity at Maximum Frown at Day 30, Full Analysis Set

|  | MT10109 10U N = 31 n (%) | MT10109 20U N = 28 n (%) | MT10109 30U N = 26 n (%) | BOTOX 20U N = 29 n (%) |
| --- | --- | --- | --- | --- |
| Live Assessment of Glabellar Lines | | | | |
| Day 30, at maximum frown | n = 30 | n = 26 | n = 25 | n = 26 |
| Responders | 18 (60.0) | 18 (69.2) | 22 (88.0) | 19 (73.1) |
| Non-responders | 12 (40.0) | 8 (30.8) | 3 (12.0) | 7 (26.9) |

Abbreviations:
N = number of subjects in analysis set;
n = number of subjects with data.
Note:
Subjects included in the analysis had to have a baseline glabellar line severity rating at maximum frown of moderate (2) or severe (3). A responder was defined as having a severity rating of none (0) or mild (1) at the corresponding post-baseline visit. Percentages are based on the number of subjects with an assessment at the relevant visit.

For the FAS, based on the investigator's live assessment of subjects' glabellar line severity at maximum frown at Day 30, the proportion of responders (a severity rating of none [0] or mild [1]) in the MT10109 20 U group was similar to that in the BOTOX® 20 U group (Table 7).

The proportion of responders in the MT10109 20 U group was 69.2% (18 of 26 subjects) and in the BOTOX® 20 U group was 73.1% (19 of 26 subjects).

There was no statistically significant difference between the proportion of responders in the MT10109 20 U and BOTOX® 20 U groups (−3.2 [95% CI: −28.3 to 21.8]; p-value 0.760) (FIG. 5).

The proportion of responders in the MT10109 10 U group was smaller compared with the BOTOX® 20 U group and the proportion of responders in the MT10109 30 U group was greater compared with BOTOX® 20 U (Table 7).

The proportion of responders in the MT10109 10 U group was 60.0% (18 of 30 subjects) and in the MT10109 30 U group was 88.0% (22 of 25 subjects) and in the BOTOX® 20 U group was 73.1% (19 of 26 subjects).

There was no statistically significant difference between the proportion of responders in the MT10109 10 U and BOTOX® 20 U groups (−9.7 [95% CI: −34.6 to 15.2]; p-value 0.448), or between the MT10109 30 U and BOTOX® 20 U groups (17.6 [95% CI: −4.1 to 39.3]; p-value 0.117) (FIG. 5).

There was no statistically significant difference between the proportion of responders in the MT10109 10 U and MT10109 20 U groups (−6.5 [95% CI: −31.4 to 18.4]; p-value 0.614), or between the proportion of responders in the MT10109 30 U and MT10109 20 U groups (20.8 [95% CI: −0.9 to 42.5]; p-value 0.066). The proportion of responders in the MT10109 10 U group was smaller than that of the MT10109 30 U group and the difference was statistically significant (−27.3 [95% CI: −48.8 to −5.8]; p-value 0.020).

The investigator's live assessment of glabellar line severity at maximum frown at Day 30 is summarized for the PP Set in Table 8. A Mantel-Haenszel chi-square test was used to compare treatment groups.

TABLE 8

Investigator's Live Assessment Rating of Glabellar Line Severity at Maximum Frown at Day 30, Per-protocol Set

| Live Assessment of Glabellar Lines | MT10109 10U N = 30 n (%) | MT10109 20U N = 26 n (%) | MT10109 30U N = 23 n (%) | BOTOX 20U N = 26 n (%) |
|---|---|---|---|---|
| Day 30, at maximum frown | n = 30 | n = 26 | n = 23 | n = 26 |
| Responders | 18 (60.0) | 18 (69.2) | 20 (87.0) | 19 (73.1) |
| Non-responders | 12 (40.0) | 8 (30.8) | 3 (13.0) | 7 (26.9) |

Abbreviations:
N = number of subjects in analysis set;
n = number of subjects with data.
Note:
Subjects included in the analysis had to have a baseline glabellar line severity rating of moderate (2) or severe (3). A responder was defined as having a severity rating of none (0) or mild (1) at the corresponding post-baseline visit. Percentages are based on the number of subjects with an assessment at the relevant visit.

The results in the PP Set supported those in the FAS.

The proportion of responders in the MT10109 20 U group was 69.2% (18 of 26 subjects) and in the BOTOX® 20 U group was 73.1% (19 of 26 subjects) (Table 8).

The difference between the proportion of responders in the MT10109 20 U and BOTOX® 20 U groups was −3.8 (95% CI: −32.8 to 25.1; p-value 0.762) which was not statistically significant.

The proportion of responders in the PP Set in the MT10109 10 U group was smaller compared with the BOTOX® 20 U group and the proportion of responders in the MT10109 30 U group was greater compared with BOTOX® 20 U:

The proportion of responders in the MT10109 10 U group was 60.0% (18 of 30 subjects) and in the MT10109 30 U group was 87.0% (20 of 23 subjects) and in the BOTOX® 20 U group was 73.1% (19 of 26 subjects) (Table 8).

There was no statistically significant difference between the proportion of 25 responders in the MT10109 10 U and BOTOX® 20 U groups (−13.1 [95% CI: −41.6 to 15.4]; p-value 0.307), or between the MT10109 30 U and BOTOX® 20 U groups (13.9 [95% CI: −12.6 to 40.3]; p-value 0.234).

Secondary Efficacy Parameter: Investigator's Rating of Glabellar Line Severity at Maximum Frown and at Rest Up to Day 120 by Live Assessment The investigator's live assessment of glabellar line severity at maximum frown and rest at other visits is summarized for the FAS in Table 9, and in diagram form in FIG. 6. A Mantel-Haenszel chi square test was used to compare treatment groups.

TABLE 9

Investigator's Live Assessment Rating of Glabellar Line Severity at Other Visits, Full Analysis Set

| Live Assessment of Glabellar Lines | MT10109 10U N = 31 n (%) | MT10109 20U N = 28 n (%) | MT10109 30U N = 26 n (%) | BOTOX 20U N = 29 n (%) |
|---|---|---|---|---|
| Day 14, at maximum frown | n = 31 | n = 28 | n = 25 | n = 28 |
| Responders | 18 (58.1) | 20 (71.4) | 22 (88.0) | 22 (78.6) |
| Non-responders | 13 (41.9) | 8 (28.6) | 3 (12.0) | 6 (21.4) |
| Day 14, at rest | n = 13 | n = 12 | n = 14 | n = 11 |
| Responders | 4 (30.8) | 3 (25.0) | 8 (57.1) | 7 (63.6) |
| Non-responders | 9 (69.2) | 9 (75.0) | 6 (42.9) | 4 (36.4) |
| Day 30, at rest | n = 12 | n = 10 | n = 13 | n = 9 |
| Responders | 4 (33.3) | 1 (10.0) | 6 (46.2) | 5 (55.6) |
| Non-responders | 8 (66.7) | 9 (90.0) | 7 (53.8) | 4 (44.4) |
| Day 60, at maximum frown | n = 30 | n = 23 | n = 25 | n = 25 |
| Responders | 15 (50.0) | 15 (65.2) | 17 (68.0) | 17 (68.0) |
| Non-responders | 15 (50.0) | 8 (34.8) | 8 (32.0) | 8 (32.0) |
| Day 60, at rest | n = 12 | n = 10 | n = 13 | n = 10 |
| Responders | 4 (33.3) | 1 (10.0) | 7 (53.8) | 4 (40.0) |
| Non-responders | 8 (66.7) | 9 (90.0) | 6 (46.2) | 6 (60.0) |
| Day 120, at maximum frown | n = 28 | n = 23 | n = 25 | n = 26 |
| Responders | 9 (32.1) | 12 (52.2) | 7 (28.0) | 6 (23.1) |
| Non-responders | 19 (67.9) | 11 (47.8) | 18 (72.0) | 20 (76.9) |
| Day 120, at rest | n = 10 | n = 10 | n = 13 | n = 10 |
| Responders | 1 (10.0) | 1 (10.0) | 5 (38.5) | 3 (30.0) |
| Non-responders | 9 (90.0) | 9 (90.0) | 8 (61.5) | 7 (70.0) |

Abbreviations:
N = number of subjects in analysis set;
n = mumber of eligible subjects with data.
Note:
Subjects included in the analysis had to have a baseline glabellar line severity rating of moderate (2) or severe (3). A responder was defined as having a severity rating of none (0) or mild (1) at the corresponding post-baseline visit. Percentages are based on the number of eligible subjects with an assessment at the relevant visit.

Figure 6:
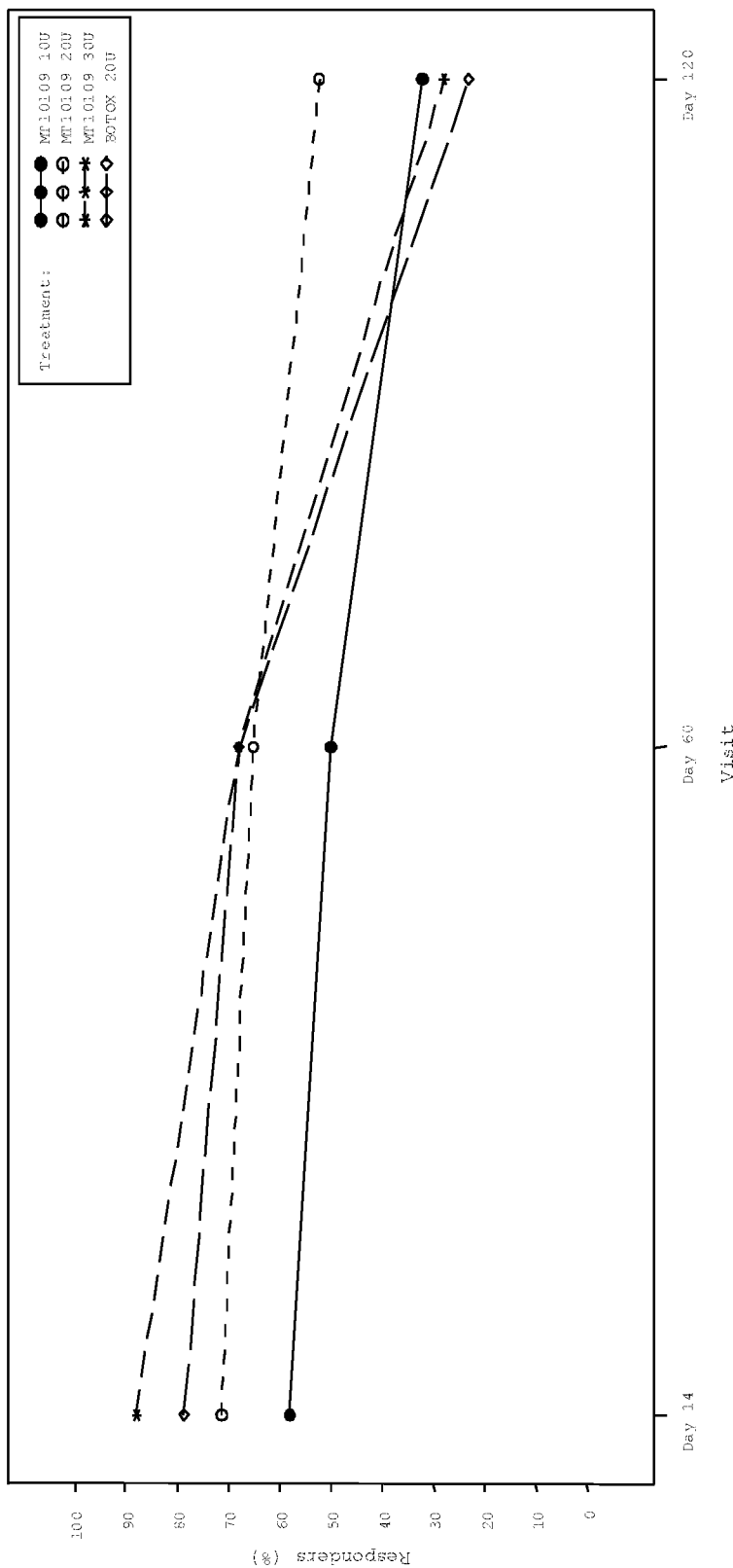
FIG. 6 is a graph depicting the percent of responders as indicated by investigator assessment rating of glabellar line severity at all visits (full analysis set). Subjects included in the analysis had to have a baseline glabellar line severity rating of moderate (2) or severe (3). A responder was defined as having a severity of none (0) or mild (1) at the corresponding post-baseline visit.

The proportion of responders at maximum frown decreased in all treatment groups from Day 14 to Day 120 (based on the investigator's live assessment). The proportions at Day 120 were greater in the MT10109 20 U group compared with BOTOX® 20 U and the other MT10109 groups (FIG. 6).

The proportion of responders at maximum frown in the MT10109 20 U group at Day 60, and at Day 120 was 65.2% (15 of 23 subjects) and 52.2% (12 of 23 subjects), respectively, and in the BOTOX® 20 U group was 68.0% (17 of 25 subjects) and 23.1% (6 of 26 subjects), respectively (Table 9).

The difference between the proportion of responders in the MT10109 20 U and BOTOX® 20 U groups at maximum frown at Day 60 was −4.3 (95% CI: −30.7 to 22.1; p-value 0.714) and at Day 120 was 24.0 (−0.7 to 48.7; p-value 0.058).

In the other MT10109 groups, the proportions of responders at maximum frown at Day 60 were smaller in the MT10109 10 U group (50.0%; 15 of 30 subjects) and similar in the MT10109 30 U group (68.0%; 17 of 25 subjects) compared with the BOTOX® 20 U group (68.0%; 17 of 25 subjects). At Day 120 proportions were greater in the MT10109 10 U (32.1%; 9 of 28 subjects) and MT10109 30 U (28.0%; 7 of 25 subjects) groups than in the BOTOX® 20 U group (23.1%; 6 of 26 subjects) (Table 9). There was no statistically significant difference in the proportion of responders at maximum frown between the MT10109 10 U and BOTOX® 20 U groups or between the MT10109 30 U and BOTOX® 20 U groups at any time point. There was no statistically significant difference in the proportion of responders at maximum frown between the MT10109 10 U and MT10109 20 U groups, or between the MT10109 30 U and MT10109 20 U groups at any time point. The proportion of responders in the MT10109 10 U group was generally smaller than in the MT10109 30 U group and the difference was statistically significant at Day 14 (−30.4 [95% CI: −55.6 to −5.2]; p-value 0.012).

In the analyses of the investigator's live assessment of glabellar line severity at rest, the number of subjects who were eligible for inclusion in the analysis (i.e., baseline glabellar line severity of either moderate [2] or severe [3]) was small. Consequently, comparisons between treatment groups and any resulting p-values should be treated with caution.

Figure 9:
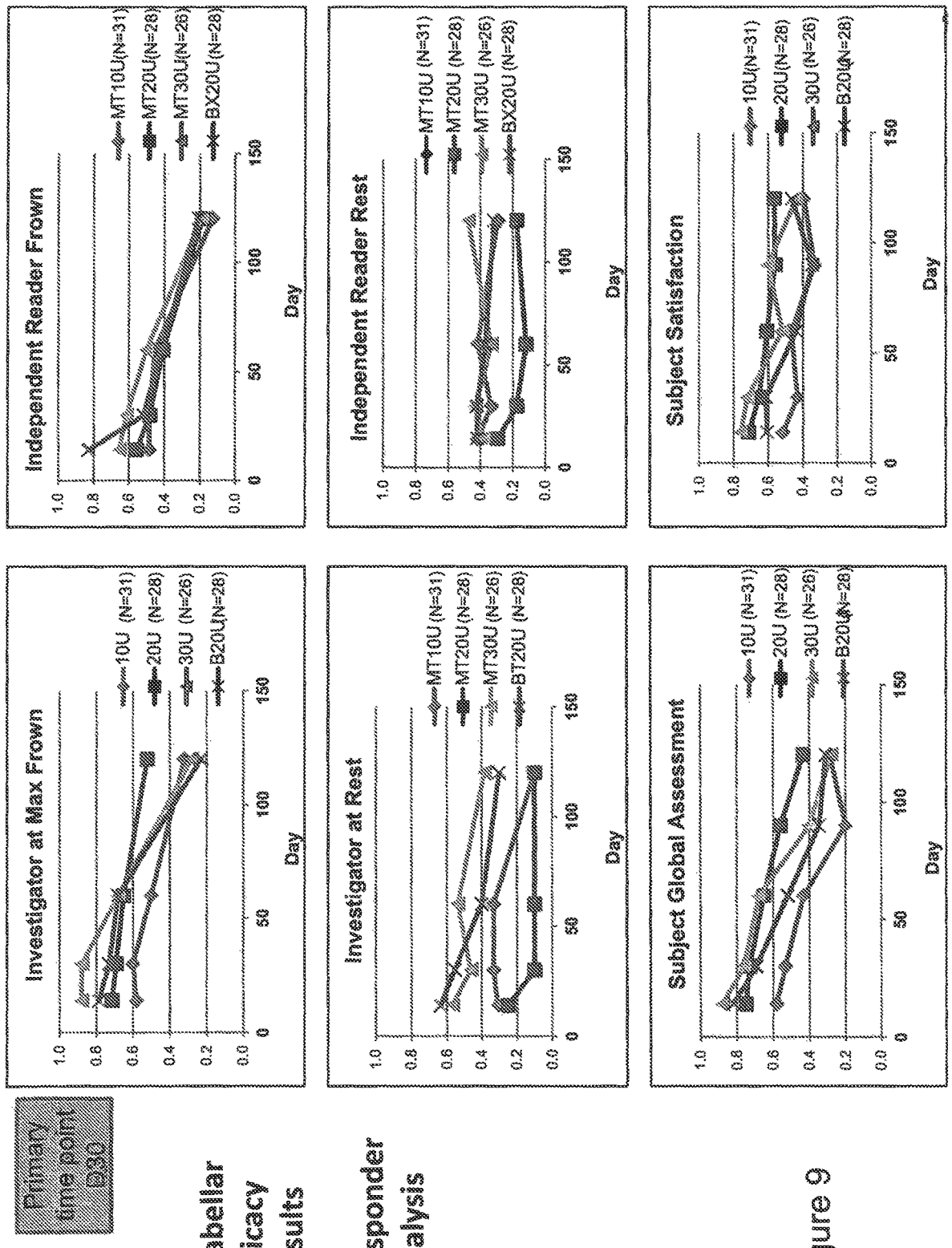
FIG. 9 is a set of graphs depicting the results of experiments. The data includes percent responding as a function of days post treatment as indicated by investigator assessment at max frown (top left), investigator assessment at rest (middle left), independent reader at frown (top right), independent reader at rest (middle right), subject global assessment (bottom left), and subject satisfaction (bottom right).

The proportion of responders at rest decreased in all treatment groups from Day 14 to Day 120 (based on the investigator's live assessment) (FIG. 9 center left). The proportions were smaller in the MT10109 20 U group compared with the BOTOX® 20 U group at every time point.

The proportion of responders at rest in the MT10109 20 U group at Day 14 and at Day 120 was 25.0% (3 of 12 subjects) and 10.0% (1 of 10 subjects), respectively, and in the BOTOX® 20 U group was 63.6% (7 of 11 subjects) and 30.0% (3 of 10 subjects), respectively (Table 9).

Proportions of responders at rest at Day 120 were smaller in the MT10109 10 U (10.0%; 1 of 10 subjects) and greater in the MT10109 30 U (38.5%; 5 of 13 subjects) groups than in the BOTOX® 20 U group (30.0%; 3 of 10 subjects) (Table 9).

Secondary Efficacy Parameter: Subject's Assessment of Glabellar Line Improvement and Satisfaction with Effect of Treatment The subject's self-assessment of glabellar line improvement is summarized in Table 10 and in diagram form in FIG. 7. The subject's self-assessment of satisfaction with the effect of treatment is summarized in Table 11 and in diagram form in FIG. 8. A Mantel-Haenszel chi square test was used to compare treatment.

TABLE 10

Subject's Self-assessment of Glabellar Line Improvement, Full Analysis Set

| Self-assessment Improvement | MT10109 10U N = 31 n (%) | MT10109 20U N = 28 n (%) | MT10109 30U N = 26 n (%) | BOTOX 20U N = 29 n (%) |
|---|---|---|---|---|
| Day 14 | n = 31 | n = 28 | n = 25 | n = 28 |
| Responders | 18 (58.1) | 21 (75.0) | 22 (88.0) | 23 (82.1) |
| Non-responders | 13 (41.9) | 7 (25.0) | 3 (12.0) | 5 (17.9) |
| Day 30 | n = 30 | n = 26 | n = 25 | n = 26 |
| Responders | 16 (53.3) | 19 (73.1) | 19 (76.0) | 18 (69.2) |
| Non-responders | 14 (46.7) | 7 (26.9) | 6 (24.0) | 8 (30.8) |
| Day 60 | n = 30 | n = 23 | n = 25 | n = 25 |
| Responders | 13 (43.3) | 15 (65.2) | 17 (68.0) | 13 (52.0) |
| Non-responders | 17 (56.7) | 8 (34.8) | 8 (32.0) | 12 (48.0) |
| Day 90 | n = 30 | n = 25 | n = 25 | n = 26 |
| Responders | 6 (20.0) | 14 (56.0) | 10 (40.0) | 9 (34.6) |
| Non-responders | 24 (80.0) | 11 (44.0) | 15 (60.0) | 17 (65.4) |
| Day 120 | n = 28 | n = 23 | n = 25 | n = 26 |
| Responders | 8 (28.6) | 10 (43.5) | 7 (28.0) | 8 (30.8) |
| Non-responders | 20 (71.4) | 13 (56.5) | 18 (72.0) | 18 (69.2) |

Abbreviations:
N = number of subjects in analysis set;
n = mumber of subjects with data.
Note:
Subjects included in the analysis had to have a baseline glabellar line severity rating of moderate (2) or severe (3). A responder was defined as having a score of at least +2 (moderate improvement, about 50%) on the 9-point scale. Percentages are based on the number of subjects with an assessment at the relevant visit.

Figure 7:
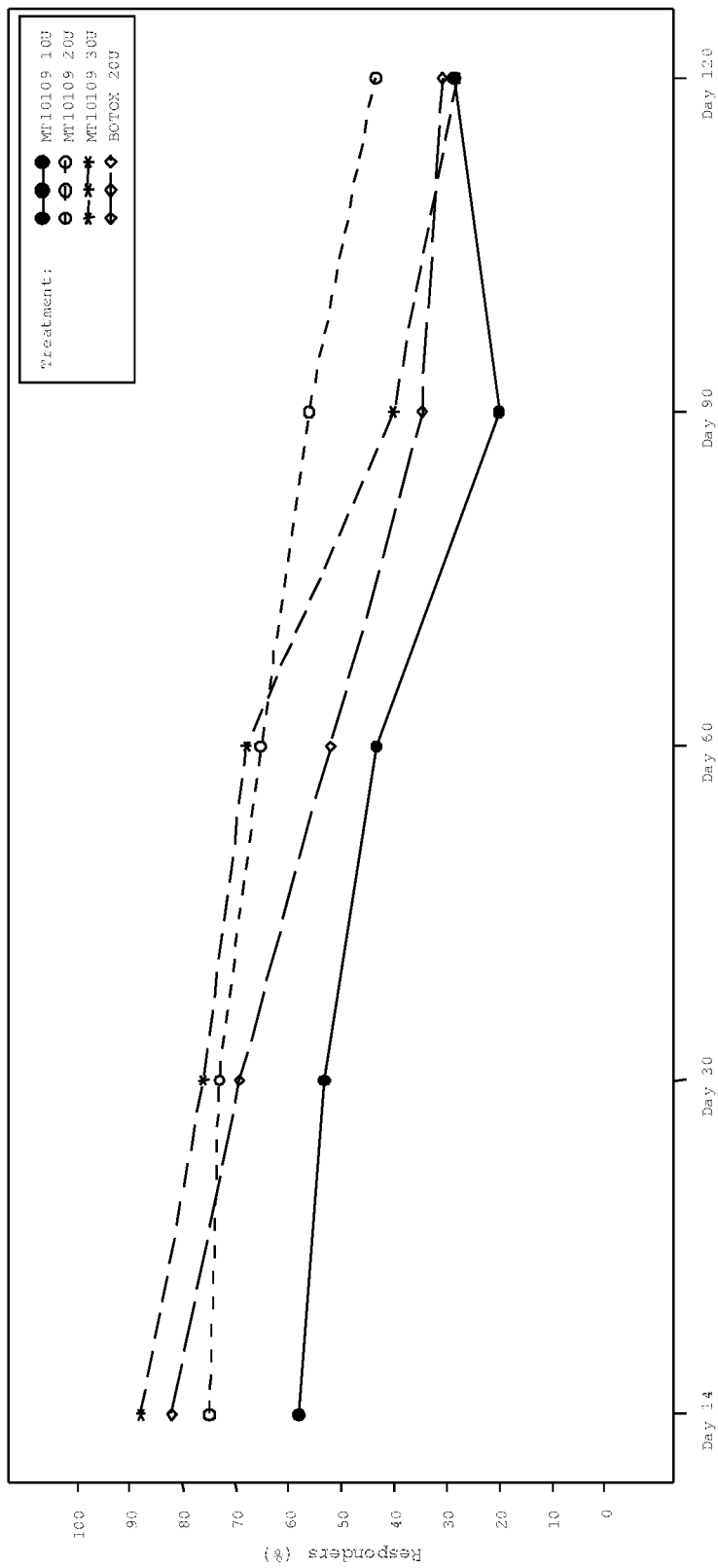
FIG. 7 is a graph depicting the percent of responders as indicated by subject's self-assessment of glabellar line improvement (full analysis set). Subjects included in the analysis had to have a baseline glabellar line severity rating of moderate (2) or severe (3). A responder was defined as having a score of at least +2 (moderate improvement, i.e., about 50%) on the 9-point scale.

In the subject's self-assessment of glabellar line improvement, the proportions of responders (a score of at least +2 [moderate improvement, about 50%] on the 9-point scale) at Day 30 were similar across the MT10109 20 U and BOTOX® 20 U groups (FAS), which reflected the live assessment ratings. The proportions were also similar across the MT10109 30 U and BOTOX® 20 U groups. At Day 60 the proportions were greater in the MT10109 20 U and MT10109 30 U groups than the BOTOX® 20 U group and at Day 120, the proportions remained greater in the MT10109 20 U group compared with the other treatment groups (FIG. 7).

The proportion of responders in the MT10109 20 U group at Day 30, Day 60 and Day 120 was 73.1% (19 of 26 subjects), 65.2% (15 of 23 subjects) and 43.5% (10 of 23 subjects), respectively, and in the BOTOX® 20 U group was 69.2% (18 of 26 subjects), 52.0% (13 of 25 subjects) and 30.8% (8 of 26 subjects), respectively (Table 10). There was no statistically significant difference between the proportion of responders in the MT10109 20 U and BOTOX® 20 U groups at any time point.

In the other MT10109 groups, at Day 30 and Day 60, proportions of responders were smaller in the MT10109 10 U group and greater in the MT10109 30 U group compared with the BOTOX® 20 U group (Table 10). At Day 120, proportions were similar across the three treatment groups (MT10109 10 U, 28.6% [8 of 28 subjects]; MT10109 30 U, 28.0% [7 of 25 subjects]; BOTOX®20 U, 30.8% [8 of 26 subjects]). The difference in the proportion of responders between MT10109 10 U and BOTOX® 20 U at Day 14 was statistically significant (−23.6 [95% CI: −46.5 to −0.6]; p-value 0.049). No statistically significant difference between the proportion of responders in the MT10109 30 U and BOTOX® 20 U groups was observed at any time point. There was no statistically significant difference in the proportion of responders in the subject's assessment of glabellar line improvement between the MT10109 30 U and MT10109 20 U groups. The proportion of responders in the MT10109 10 U group was smaller than in the other two groups at each time point. The difference was statistically significant between the MT10109 10 U and MT10109 30 U groups at Day 14 (−30.4 [95% CI: −52.0 to −8.7]; p-value 0.011) and between the MT10109 10 U and MT10109 20 U groups at Day 90 (−34.7 [95% CI: −58.8 to −10.7]; p-value 0.007).

TABLE 11

Subject's Self-assessment of Satisfaction with the Effect of the Treatment, Full Analysis Set

| Self-assessment Satisfaction | MT10109 10U N = 31 n (%) | MT10109 20U N = 28 n (%) | MT10109 30U N = 26 n (%) | BOTOX 20U N = 29 n (%) |
|---|---|---|---|---|
| Day 14 | n = 31 | n = 28 | n = 25 | n = 28 |
| Responders | 16 (51.6) | 20 (71.4) | 19 (76.0) | 17 (60.7) |
| Non-responders | 15 (48.4) | 8 (28.6) | 6 (24.0) | 11 (39.3) |
| Day 30 | n = 30 | n = 26 | n = 25 | n = 26 |
| Responders | 13 (43.3) | 17 (65.4) | 18 (72.0) | 16 (61.5) |
| Non-responders | 17 (56.7) | 9 (34.6) | 7 (28.0) | 10 (38.5) |
| Day 60 | n = 30 | n = 23 | n = 25 | n = 25 |
| Responders | 14 (46.7) | 14 (60.9) | 13 (52.0) | 11 (44.0) |
| Non-responders | 16 (53.3) | 9 (39.1) | 12 (48.0) | 14 (56.0) |
| Day 90 | n = 30 | n = 25 | n = 25 | n = 26 |
| Responders | 10 (33.3) | 14 (56.0) | 15 (60.0) | 9 (34.6) |
| Non-responders | 20 (66.7) | 11 (44.0) | 10 (40.0) | 17 (65.4) |
| Day 120 | n = 28 | n = 23 | n = 25 | n = 26 |
| Responders | 11 (39.3) | 13 (56.5) | 11 (44.0) | 12 (46.2) |
| Non-responders | 17 (60.7) | 10 (43.5) | 14 (56.0) | 14 (53.8) |

Abbreviations:
N = number of subjects in analysis set;
n = number of subjects with data.
Note:
Subjects included in the analysis had to have a baseline glabellar line severity rating of moderate (2) or severe (3). A responder was defined as having a score of at least 6 (satisfied) on the 7-point scale. Percentages are based on the number of subjects with an assessment at the relevant visit.

In the subject's self-assessment of satisfaction with the effect of treatment, a responder was defined as having a score of at least 6 (satisfied) on the 7-point scale.

Figure 8:
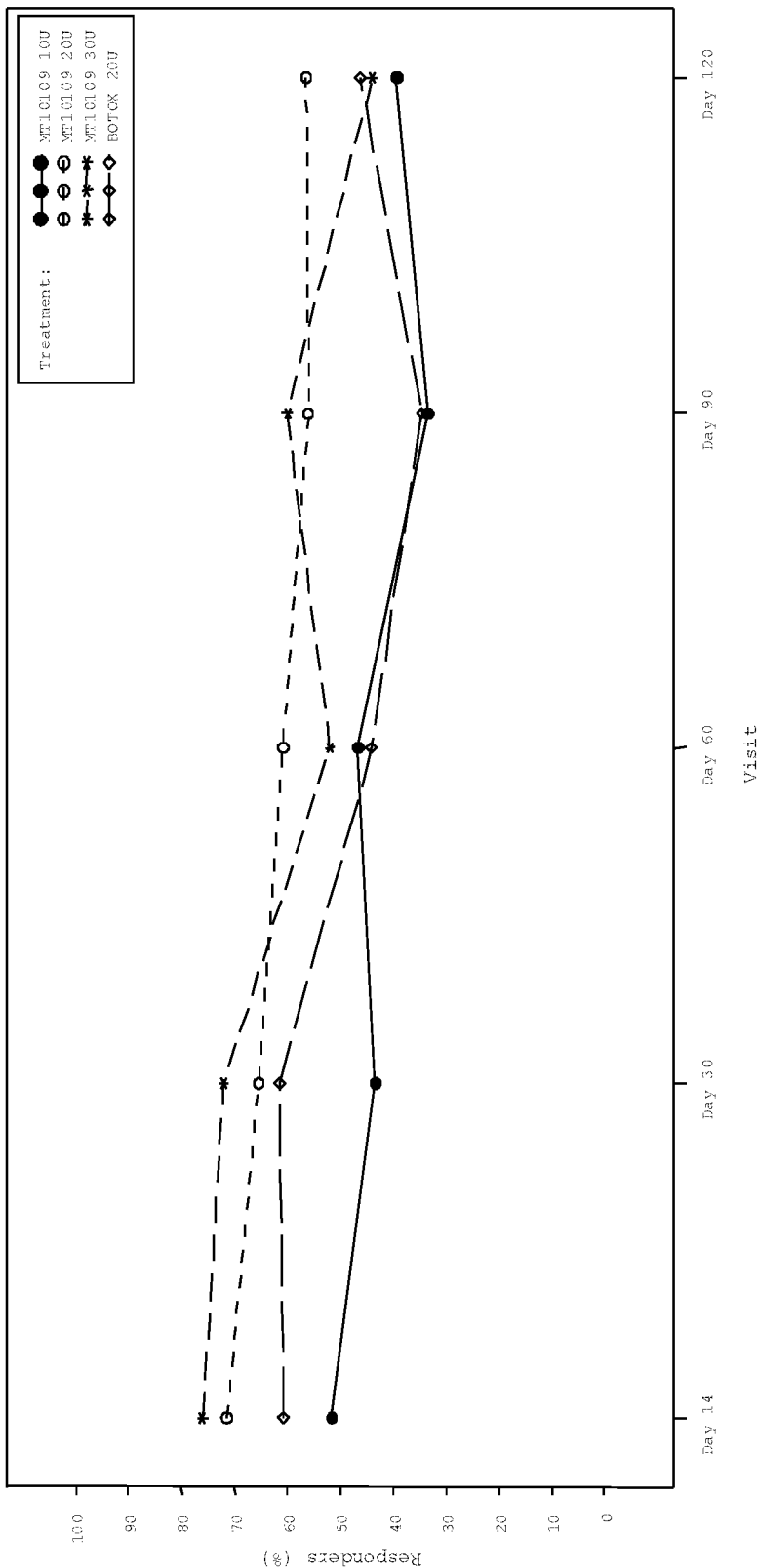
FIG. 8 is a graph depicting the percent of responders as indicated by subject's self-assessment of satisfaction with the effect of treatment (full analysis set). Subjects included in the analysis had to have a baseline glabellar line severity rating of moderate (2) or severe (3). A responder was defined as having a score of at least 6 (satisfied) on the 7-point scale.

As seen in the self-assessment of improvement, the proportion of responders in the assessment of satisfaction at Day 30 were similar in both the MT10109 20 U and BOTOX® 20 U groups, which reflected the live assessment ratings. At Day 120, the responder rate was greater in the MT10109 20 U group than any other treatment group (FIG. 8). Satisfaction appeared consistent in the MT10109 20 U group but a pattern was hard to discern in the BOTOX® 20 U and other MT10109 groups.

The proportion of responders in the MT10109 20 U group at Day 30, Day 60 and Day 120 was 65.4% (17 of 26 subjects), 60.9% (14 of 23 subjects) and 56.5% (13 of 23 subjects), respectively, and in the BOTOX® 20 U group was 61.5% (16 of 26 subjects), 44.0% (11 of 25 subjects) and 46.2% (12 of 26 subjects), respectively (Table 11). There was no statistically significant difference in the proportion of responders between the MT10109 20 U and BOTOX®20 U groups at any time point.

In the other MT10109 groups, at Day 30, proportions of responders were smaller in the MT10109 10 U group and greater in the MT10109 30 U group compared with the BOTOX® 20 U group (Table 11). At Day 60, proportions were greater in both MT10109 groups compared with BOTOX® 20 U. At Day 120, proportions were smaller in the MT10109 10 U (39.3% [11 of 28 subjects]) and MT10109 30 U (44.0% [11 of 25 subjects]) treatment groups compared with the BOTOX®20 U group (46.2% [12 of 26 subjects]). No statistically significant difference in the proportion of responders between the MT10109 10 U and BOTOX® 20 U groups or the MT10109 30 U and BOTOX® 20 U groups was observed at any time point.

There was no statistically significant difference in the proportion of responders in the subject's assessment of satisfaction with the effect of treatment between the MT10109 10 U and MT10109 20 U groups, or between the MT10109 30 U and MT10109 20 U groups. The proportion of responders in the MT10109 10 U group was smaller than in the MT10109 30 U group at each time point and the difference was statistically significant at Day 30 (−27.3 [95% CI: −52.8 to −1.9]; p-value 0.040).

Efficacy Results (FAS)—Improved Sustained Efficacy of MT10109

MT10109 at a single dose of 20 U demonstrated a similar effect to that of BOTOX® 20 U in reducing subjects' glabellar lines.

After the investigator's live assessment of glabellar line severity at maximum frown at Day 30, the proportion of responders in the MT10109 20 U group was 69.2% and in the BOTOX® 20 U group was 73.1%. The difference between the proportion of responders in the two treatment groups was −3.2 (95% CI: −28.3 to 21.8) which was not statistically significant (p-value 0.760).

In the subject's self-assessment of glabellar line improvement and satisfaction with the effect of treatment, proportions of responders were generally greater in the MT10109 20 U and MT10109 30 U groups compared with BOTOX® 20 U. At Day 30, responder rates in the MT10109 20 U and BOTOX® 20 U groups were similar, reflecting the live assessment ratings (MT10109 20 U group, 73.1% for improvement and 65.4% for satisfaction with treatment effect; BOTOX® 20 U group, 69.2% and 61.5%, respectively).

The response at maximum frown was sustained in the MT10109 20 U group to Day 120. The proportion of responders at Day 120, according to the investigator's live assessment, was 52.2% in the MT10109 20 U group compared with 23.1% in the BOTOX® 20 U group. At most time points, proportions of responders at maximum frown were greater in the MT10109 30 U group and smaller in the MT10109 10 U group compared with the BOTOX® 20 U group.

Fewer subjects were considered responders by the independent reviewers based on the photographic assessment; however, the proportions of responders (using the mean score) at maximum frown at Day 30 and Day 60 were similar in the MT10109 20 U (48.1% and 40.7%, respectively) and BOTOX® 20 U treatment groups (51.7% and 41.4%, respectively), which reflected the investigator's live assessment.

In both the investigator's live assessment and independent reviewers' photographic assessment of glabellar lines severity at rest, the proportions of responders were small across all treatment groups. At most time points, the responder rates were smaller in the MT10109 20 U group compared with the BOTOX® 20 U group.

Using a logistic regression at Day 30 and at maximum frown, the dose-response curve showed no relationship between dose and response.

Figure 10:
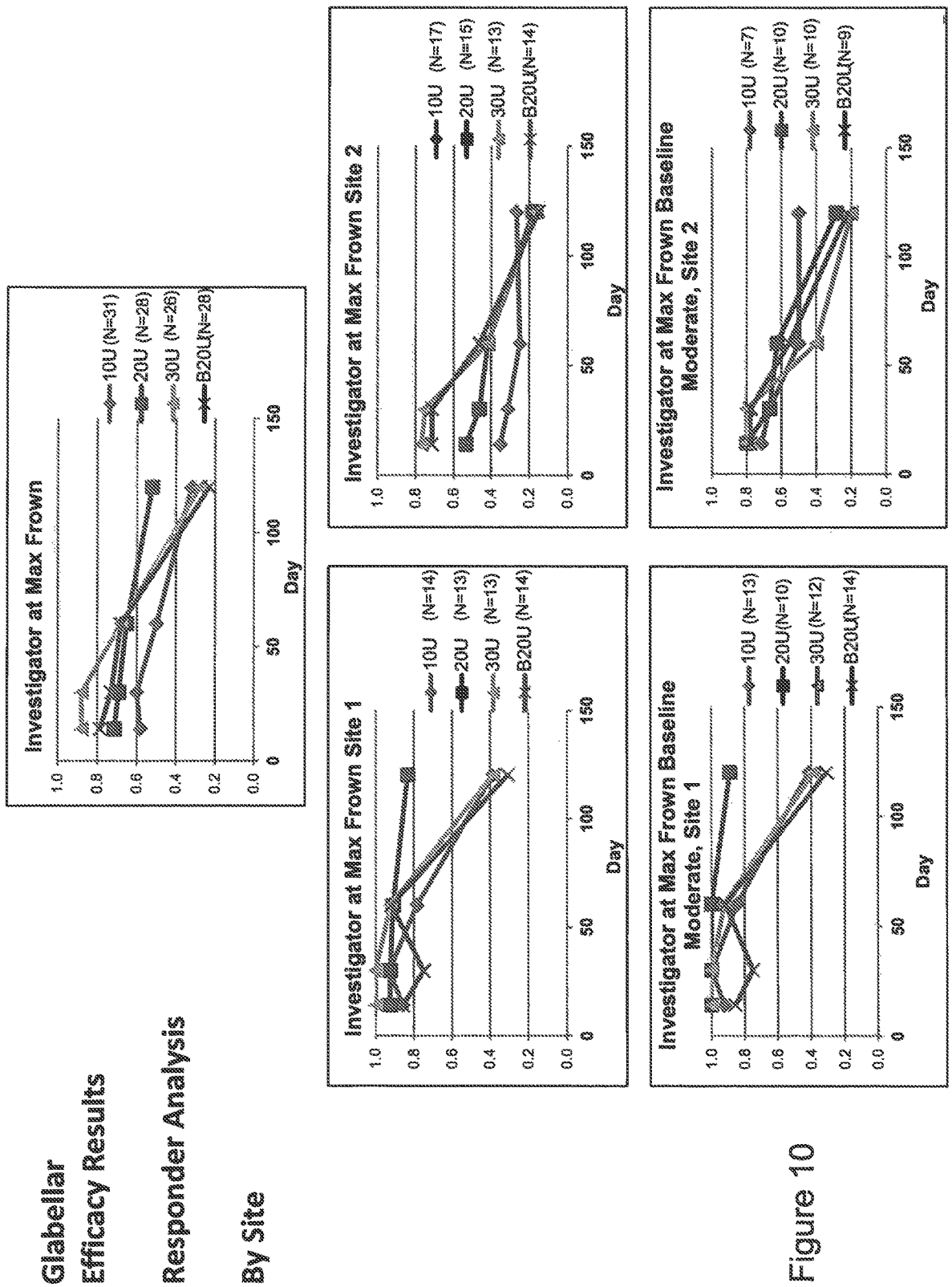
FIG. 10 is a set of graphs depicting the results of experiments. The data includes the percent responding as indicated by investigator at max frown. The top graph displays the collective data. The graphs at middle left and bottom left represent the data from site 1, while the graphs at middle right and bottom right represent the data from site 2.

The data from the experiments is further illustrated in FIG. 9 and FIG. 10. FIG. 9 presents a series of graphs depicting investigator assessment at maximum frown and at rest, independent reader assessment at maximum frown and at rest, and the subjects' assessment and satisfaction. FIG. 10 illustrates the data as generated collectively, and broken into the two different treatment sites.

In summary, the data presented herein demonstrate that lyophilized MT10109 dosed at 20 U demonstrates similarity to BOTOX® at early time points (e.g. day 30). Further, it is demonstrated that MT10109 dosed at 20 U displays an increased sustained effect compared to BOTOX®, as the response of treatment was seen to be increased in the MT10109 20 U group compared to BOTOX® 20 U group at 120 days post treatment.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method for treating a condition in a patient in need thereof, the method comprising the step of locally administering a therapeutically effective amount of an animal-protein-free botulinum toxin composition, whereby a symptom of the condition is thereby effectively alleviated for a period of time longer than that of an animal-protein-containing botulinum toxin composition, and wherein the condition is facial line.

2. The method of claim 1, wherein the animal-protein-free botulinum toxin composition is in a form selected from the group consisting of a liquid composition and a lyophilized composition.

3. The method of claim 2, wherein the liquid composition comprises botulinum toxin, polysorbate, and amino acid.

4. The method of claim 2, wherein the lyophilized composition comprises botulinum toxin, polysorbate, and amino acid, and one or more components selected from the group consisting of a sugar, a sugar alcohol, and an ionic compound.

5. The method of claim 1, wherein the animal-protein-free botulinum toxin composition persists in the patient for a period longer than that of an animal-protein-containing botulinum toxin composition.

6. The method of claim 1, wherein the facial line is hyperfunctional facial line.

7. The method of claim 6, wherein the animal-protein-free composition provides effective alleviation for a period of time of at least 16 weeks.

8. A method for treating a condition in a patient in need thereof, the method comprising the step of locally administering a therapeutically effective amount of an animal-protein-free botulinum toxin composition, wherein the composition is administered at an interval of time between a first treatment and a second treatment effective to maintain alleviation of at least one symptom of the condition, that is greater than the interval of time for an animal-protein-containing botulinum toxin composition dosed at the same amount and administered in the same manner and to the same location(s) as that of the animal-protein-free composition, and wherein the condition is facial line.

9. The method of claim 8, wherein the animal-protein-free botulinum toxin composition is in a form selected from the group consisting of a liquid pharmaceutical composition and a pharmaceutical lyophilized preparation.

10. The method of claim 9, wherein the liquid pharmaceutical composition comprises botulinum toxin, polysorbate, and amino acid.

11. The method of claim 9, wherein the pharmaceutical lyophilized preparation comprises botulinum toxin, polysorbate, and amino acid, and one or more components selected from the group consisting of a sugar, a sugar alcohol, and an ionic compound.

12. The method of claim 8, wherein the interval of time between a first treatment and a second treatment is greater than 3 months.

13. A method to reduce frequency of treatment with botulinum toxin for a condition in a patient thereby affected, comprising:
    providing an animal-protein free botulinum toxin composition for local administration by injection at a treatment site, wherein administration of a first therapeutically effective amount is separated by a time interval from administration of a second therapeutically effective amount, said time interval being greater than a time interval between first and second treatment of a therapeutically effective amount of an animal-protein containing botulinum toxin composition administered by injection at the treatment site, and wherein the condition is facial line.

14. The method of claim 13, wherein the animal-protein free botulinum toxin composition has a greater length of effect compared to the animal-protein containing botulinum toxin composition.

15. The method of claim 13, wherein the time interval between first and second treatment of the animal-protein free botulinum toxin composition is greater than about 16 weeks.

16. The method of claim 13, wherein the facial line is hyperfunctional facial line.

17. The method of claim 13, wherein the animal-protein-free botulinum toxin composition is in a form selected from the group consisting of a liquid pharmaceutical composition and a pharmaceutical lyophilized preparation.

18. The method of claim 17, wherein the liquid pharmaceutical composition comprises botulinum toxin, polysorbate, and amino acid.

19. The method of claim 17, wherein the pharmaceutical lyophilized preparation comprises botulinum toxin, polysorbate, and amino acid, and one or more components selected from the group consisting of a sugar, a sugar alcohol, and an ionic compound.

* * * * *